United States Patent [19]

Nishihara et al.

[11] Patent Number: 5,039,867
[45] Date of Patent: Aug. 13, 1991

[54] THERAPEUTIC APPARATUS

[75] Inventors: Susumu Nishihara; Kazuhiro Ueda, both of Amagasaki, Japan

[73] Assignee: Mitsubishi Denki Kabushiki Kaisha, Tokyo, Japan

[21] Appl. No.: 637,950

[22] Filed: Jan. 8, 1991

Related U.S. Application Data

[63] Continuation of Ser. No. 235,981, Aug. 24, 1988, abandoned.

[30] Foreign Application Priority Data

| Aug. 24, 1987 | [JP] | Japan | 62-208344 |
| Aug. 24, 1987 | [JP] | Japan | 62-210915 |
| Oct. 8, 1987 | [JP] | Japan | 62-153326 |
| Oct. 12, 1987 | [JP] | Japan | 62-256975 |
| Nov. 5, 1987 | [JP] | Japan | 62-278218 |
| Nov. 17, 1987 | [JP] | Japan | 62-288495 |
| Dec. 10, 1987 | [JP] | Japan | 62-310936 |
| Feb. 17, 1988 | [JP] | Japan | 63-32642 |

[51] Int. Cl.[5] .............................................. A61N 5/10
[52] U.S. Cl. .............................. 250/492.3; 250/491.1; 378/205; 378/65; 378/69
[58] Field of Search ............... 250/491.1, 492.3, 492.1; 378/205, 65, 69

[56] References Cited

U.S. PATENT DOCUMENTS

| 3,783,251 | 1/1974 | Pavkovich | 235/151 |
| 3,794,840 | 2/1974 | Scott | 250/363 |
| 4,118,631 | 10/1978 | Froggatt | 378/65 |
| 4,365,341 | 12/1982 | Lam | 378/65 |
| 4,609,940 | 9/1986 | Born et al. | 378/205 |
| 4,829,986 | 5/1989 | Eichler et al. | 378/205 |

FOREIGN PATENT DOCUMENTS

| 1133501 | 7/1962 | Fed. Rep. of Germany . |
| 2218237 | 11/1972 | Fed. Rep. of Germany . |
| 2300887 | 7/1974 | Fed. Rep. of Germany . |
| 2317748 | 10/1974 | Fed. Rep. of Germany . |
| 1412685 | 11/1975 | United Kingdom . |

OTHER PUBLICATIONS

"Conventional X-ray Imaging", by J. A. Garrett, et al, IEE Proceedings, vol. 134, Pt. A, No. 2, Feb. 1987, pp. 107-114.
"Digital X-ray Imaging", by B. M. Moores, IEE Proceedings, vol. 134, Pt. A, No. 2, Feb. 1987, pp. 115-125.
Translation of DE-AS 1133501, Col. 1, line 37 through Col. 2, line 45.
Physics and Medicine: The Bevatron/Bevalac Experience; IEEE Transactions.
Operations Experience at the Bevalac Radiotherapy Facility; IEEE Transactions.
Wobbler Facility for Biomedical Experiments at the Bevalac, IEEE Transactions.
Phase-Locked Loop: General Information; The Motorola Semiconductor Products Publication.
The Phase-Lock Techniques Publication.

*Primary Examiner*—Jack I. Berman

[57] ABSTRACT

A method and apparatus for positioning a therapeutic beam in which a first distance from a first predetermined position other than an affected part of a patient to the affected part, is determined on the basis of a first image which includes at least part of the patient and which includes the position of the affected part of the patient. A second distance, from a second predetermined position corresponding to the first predetermined position to a position of the therapy beam, is determined on the basis of a second image which includes at least part of the patient and which indicates the position of the therapy beam. The patient is then moved such that the therapy beam is irradiated onto the affected part, on the basis of the first distance and the second distance.

6 Claims, 30 Drawing Sheets (A) REFERENCE IMAGE (B) X-RAY TV IMAGE (A) REFERENCE IMAGE (B) X-RAY TV IMAGE

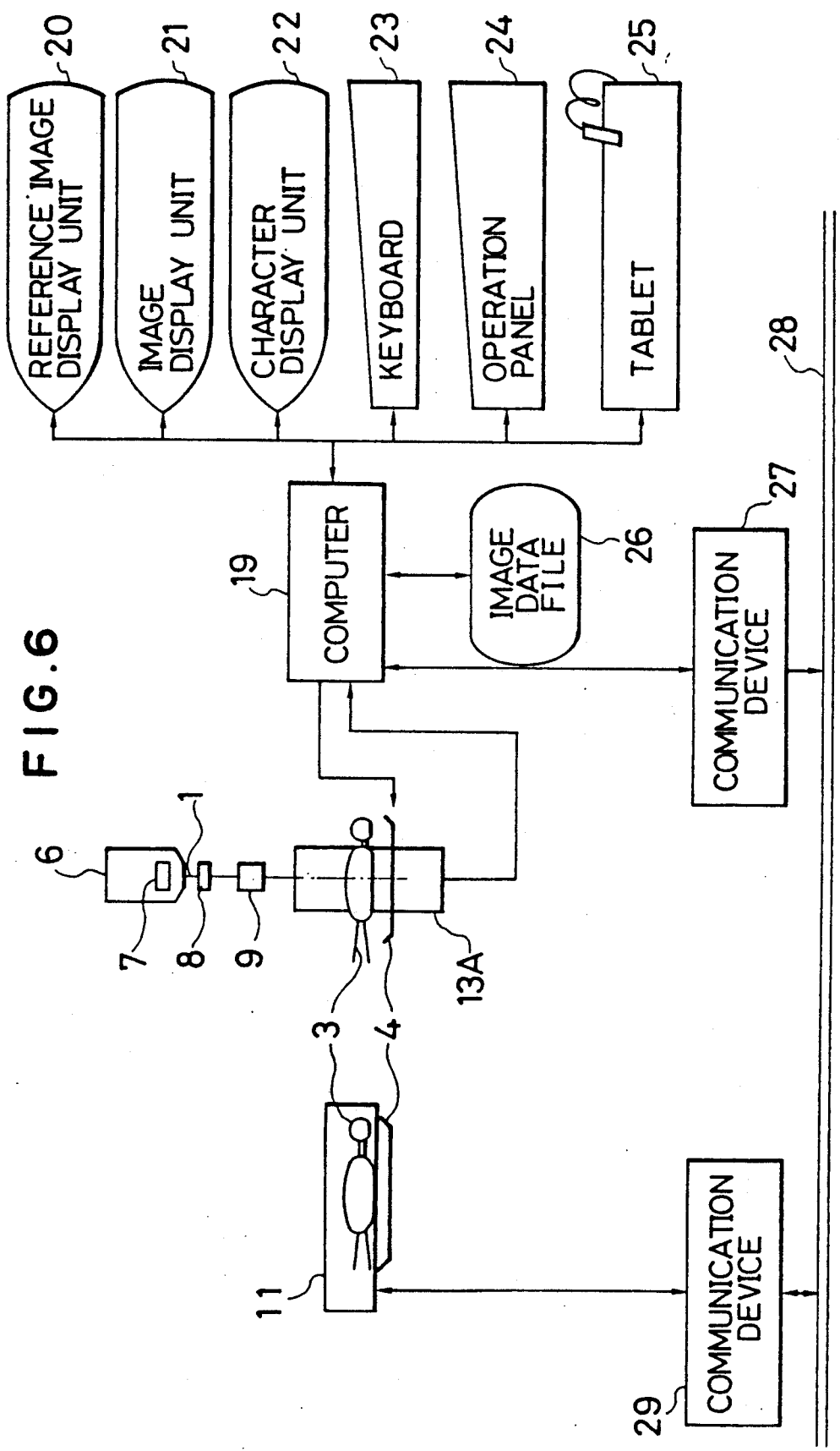

Z-AXIS
REFERENCE IMAGE

Z-AXIS
X-RAY CT SLICE IMAGE

F I G. 14
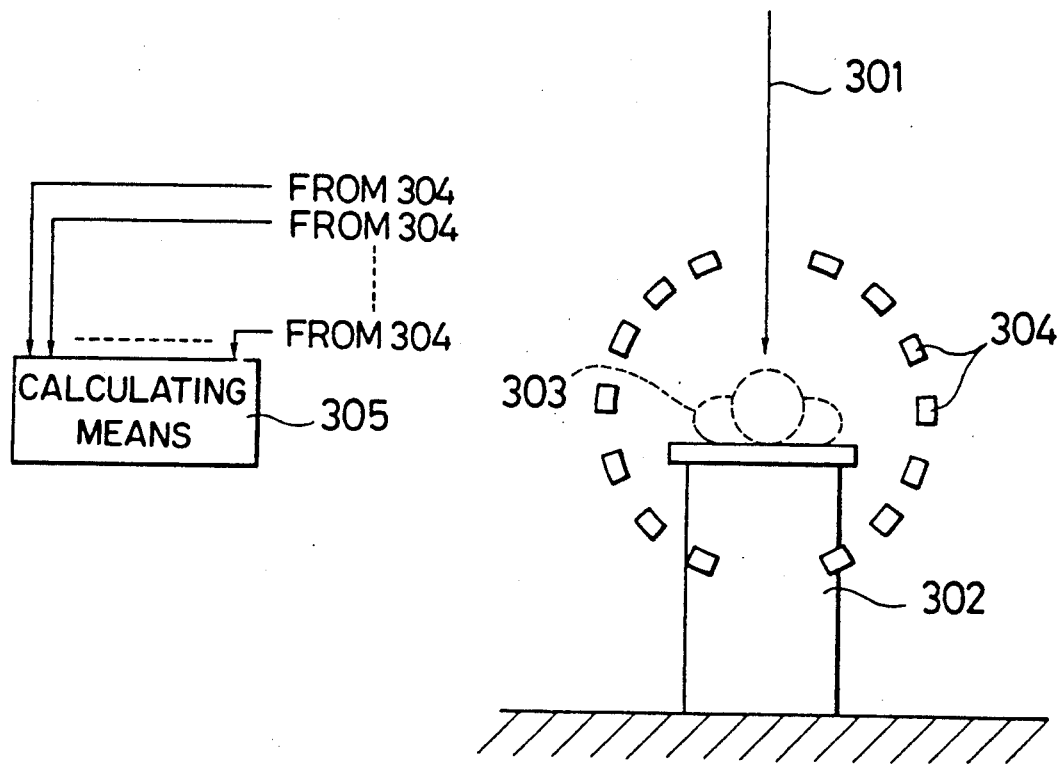
F I G. 15
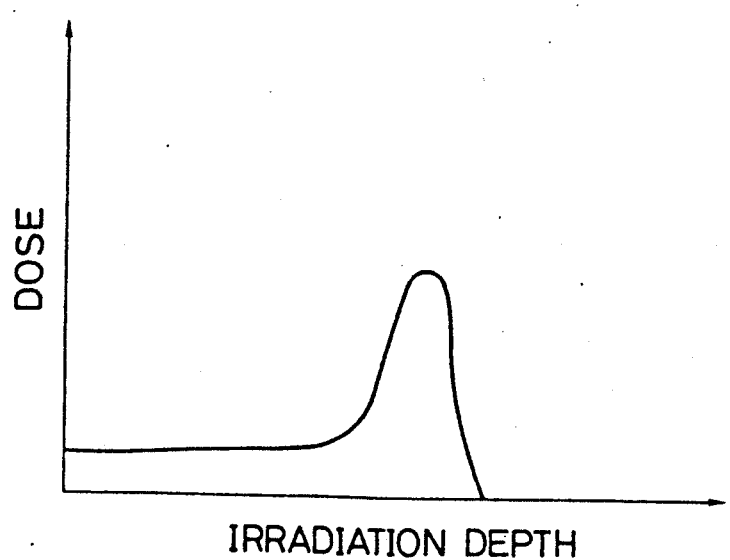

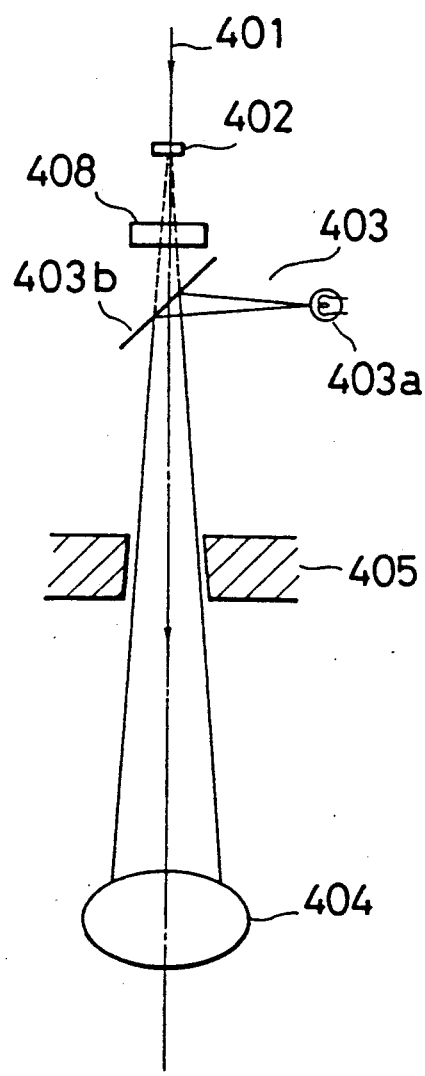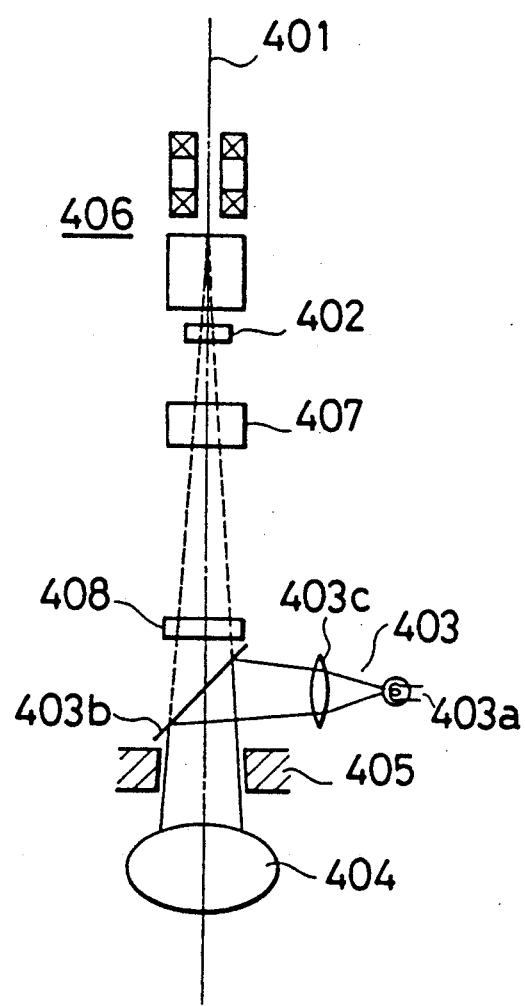
FIG.16
FIG.17

TARGET REGION

5,039,867

THERAPEUTIC APPARATUS

This application is a continuation, of application Ser. No. 07/235,981 filed on Aug. 24, 1988, now abandoned.

BACKGROUND OF THE INVENTION

The present invention relates to a therapeutic apparatus including a therapeutic radiation source emitting a therapeutic radiation beam such as an ionized particle beam (beam of ionized particles), a heavy particle beam (baryon beam) or a neutron beam, for irradiation onto the part of the patient affected by a malignant tumor, such as cancer (carcinoma).

In this type of therapeutic apparatus, the therapeutic radiation beam, e.g., ionized particle beam, accelerated by a cyclotron is guided to the therapy room where the patient is fixed to a therapy table such as a therapy chair or a therapy bed. Prior to irradiation, the therapy table must be positioned accurately such that the affected part is in alignment with the therapeutic radiation beam. It is desirable that this positioning be made in a simple manner and in a short time. The radiation dose must be accurately controlled. The area of irradiation must be accurately defined such that the irradiation field coincides with the extension of the affected part. The energy of the beam must also be controlled and varied during irradiation such that the range, i.e., the depth of irradiation or penetration into the patient, matches the location and extension of the affected part within the body of the patient.

Prior art therapeutic apparatuses of this type were not satisfactory with respect to one or more of the above requirements.

SUMMARY OF THE INVENTION

An object of the invention is to provide improvements in a therapeutic apparatus.

Another object of the invention is to provide a therapeutic apparatus which meets various requirements set forth above.

Another object of the invention is to enable accurate and quick positioning of the patient with respect to the therapeutic radiation beam.

Another object of the invention is to enable accurate control over irradiation dose.

Another object of the invention is to enable accurate definition of the beam.

Another object of the invention is to enable accurate control and variation of the energy of the therapeutic radiation beam.

Another object of the invention is to provide a uniform dose distribution of an ionized particle beam over an enlarged irradiation field.

Another object of the invention is to provide an iris for the ionized particle beam with equal effectiveness for all directions.

Another object of the invention is to enable detection of the location at which the irradiation actually occurs.

Another object of the invention is to enable positioning of the light field localizer nearer to the patient.

Another object of the invention is to reduce the loss of the energy of a particle beam in the measurement of the particle beam.

Another object of the invention is to improve the accuracy of the monitoring of a particle beam.

Another object of the invention is to provide a range adjuster having an absorption member of which the thickness can be varied continuously.

Another object of the invention is to eliminate the necessity of providing a ridge filter and a bolus for individual patients.

Another object of the invention is to enable three-dimensional irradiation of a particle beam in conformity with the shape of the affected part.

Another object of the invention is to provide a uniform dose distribution with respect to the depth within the body.

Another object of the invention is to provide a bed which eliminates the need of moving the patient between the diagnosis using a slice image pick-up device and irradiation therapy using a particle beam therapeutic apparatus.

According to the invention there is provided a therapeutic apparatus comprising:
  irradiating means for irradiating a therapy beam;
  a therapy table on which a patient is mounted;
  first image pick-up means for picking up an image of at least part of the patient indicating the position of an affected part;
  first display means for displaying a first image taken by said first image pick-up means;
  second image pick-up means for picking up an image of at least part of the patient indicating the position of the therapy beam;
  second display means for displaying a second image taken by said second image pick-up means;
  input means for inputting positional information of the affected part for indication in said first image and said second image;
  computing means for calculating the distance of movement of the therapy table such that the therapy beam is irradiated onto the affected part of the patient on the basis of said first image and said second image with said positional information; and
  means for moving said patient relative to said therapy beam on the basis of the calculated distance.

According to another aspect of the invention, there is provided a method of positioning a therapeutic beam comprising the steps of:
  determining a first distance from a first predetermined position other than an affected part of a patient to the affected part on the basis of a first image including at least part of the patient and indicating the position of the affected part of the patient;
  determining a second distance from a second predetermined position corresponding to said first predetermined position to a position of the therapy beam on the basis of a second image including at least part of the patient and indicating the position of the therapy beam; and
  moving the patient such that the therapy beam is irradiated onto the affected part, on the basis of said first distance and said second distance.

According to another aspect of the invention, there is provided an ionized particle beam apparatus comprising:
  first and second scanning electromagnets for deflecting an ionized particle beam in directions orthogonal to each other;
  means for applying AC currents to said first and second scanning electromagnets to generate a rotating magnetic field thereby to rotate said ionized particle beam, said ionized particle beam being irradiated in an irradiation field; and a scattering member disposed on the path of said ionized particle beam, either upstream or downstream of said first and second scanning electromagnets for enlarging the radius of the area over which said ionized particle beam is irradiated.

According to another aspect of the invention, there is provided an ionized particle beam apparatus comprising:

slit assembly means having pairs of slit pieces, the slit pair of each pairs being movable back and forth opposite to each other to adjust the size of the beam that is irradiated onto an irradiated part;

an aperture defined by the inner edges of slit pieces determining the profile of the ionized particle beam; and means for moving the slit pieces of each pair toward and away from each other, wherein the inner edge of each of the slit pieces are generally concave toward the center of the aperture.

According to another aspect of the invention, there is provided an ionized particle beam cancer therapeutic apparatus comprising:

means for irradiating an ionized particle beam onto a cancer affected part;

means for changing the configuration of the irradiation field;

a light source for use in confirmation of the changed irradiation field; and a lens system disposed between the light source and the patient, whereby the light source is disposed near the patient.

According to another aspect of the invention, there is provided a particle beam monitor device comprising:

an insulating plate;

a high-voltage electrode; and a collector electrode disposed opposite to said high-voltage electrode with the insulating plate interposed between them in a housing filled with a gas, wherein said collector electrodes are formed by plating or evaporating metal on a resin plate.

According to another aspect of the invention, there is provided a particle beam monitor device comprising:

an insulating plate;

a high-voltage electrode; and a collector electrode disposed opposite to said high-voltage electrode with the insulating plate interposed between them in a housing filled with a gas, said collector electrode being formed by plating or evaporating metal on a resin plate;

an additional collector electrode formed by plating or evaporating metal on a resin plate; and an additional high-voltage electrode positioned opposite to said additional collector electrode with an insulating plate interposed between them.

According to another aspect of the invention, there is provided a range adjuster for use in a particle beam therapeutic apparatus for irradiating an ionized particle beam for killing cancer cells comprising:

first and second wedge-shaped energy absorption members stacked with each other, with the directions in which said wedge-shaped members being tapered and opposite to each other; and means for moving the wedge-shaped members back and forth in the directions in which said wedge-shaped members are tapered to vary the total thickness of the absorption members through which the particle beam must pass.

According to another aspect of the invention, there is provided an ionized particle beam cancer therapy apparatus for irradiating an ionized particle beam onto a cancer affected part for the purpose of therapy, comprising:

a range shifter for varying the energy of ionized particle beam; and a collimator for varying the shape of the irradiation in a plane perpendicular to the path of the beam, said range shifter and said collimator being disposed on the path of the beam, whereby the three-dimensional irradiation is conducted in conformity with the shape of the affected part.

According to another aspect of the invention, there is provided a method of irradiating an ionized particle beam in which irradiation is successively made for different depths, comprising the steps of:

using a radiation beam having a range peak at a certain depth and a lower range distribution in the shallower part; and giving smaller irradiation does for shallower parts so that the total dose taking account of the lower distribution at the part shallower than the position of the range peak is constant throughout the entire depth of the affected part.

According to another aspect of the invention, there is provided a therapy/diagnosis bed comprising:

a bed main body on which a patient is mounted; and means for moving said bed main body between a medical slice image pick-up device and a particle beam therapy apparatus, with said patient fixed to said bed main body, whereby diagnosis by use of said medical slice image pick-up device and therapy by use of said particle beam therapy apparatus are both enabled.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 6 is a schematic diagram showing a therapeutic apparatus according to another embodiment of the invention.

FIG. 14 shows an apparatus for measuring the dose and/or location of the irradiation.

FIG. 15 shows an example of absorption dose distribution of the ionized particle beam.

FIG. 16 is an elevational view showing another embodiment of an ionized particle beam therapeutic apparatus.

FIG. 17 is an elevational view showing another embodiment of an ionized particle beam therapeutic apparatus.

DETAILED DESCRIPTION OF THE PREFERRED EMBODIMENTS

Figure 1:
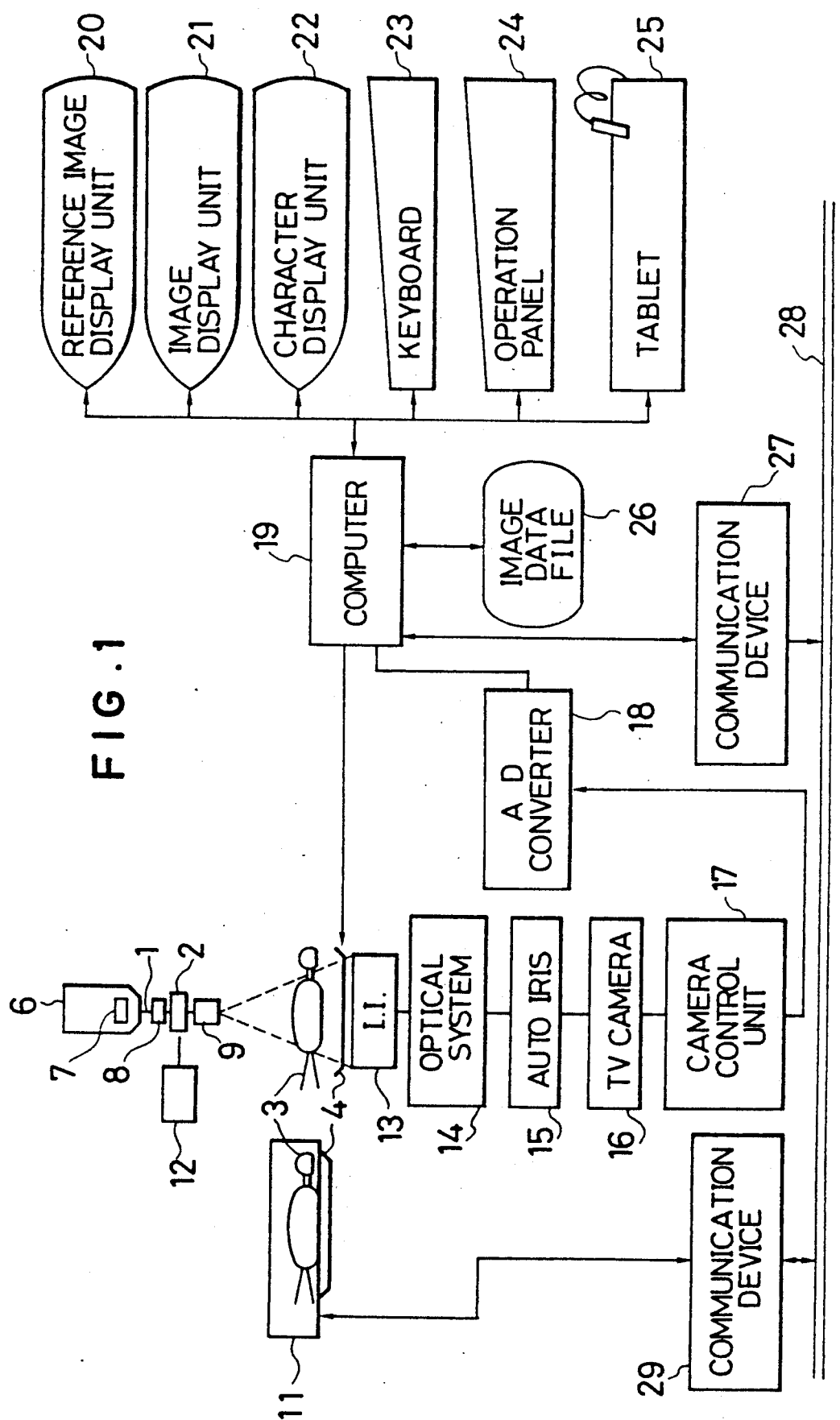
FIG. 1 is a schematic diagram showing a therapeutic apparatus according to an embodiment of the invention.

FIG. 1 shows an embodiment of a therapeutic apparatus according to the invention. As illustrated, it comprises an irradiation apparatus including a vertical irradiation unit 6, a range shifter 7, a dose monitor 8, and a collimator 9, which are aligned along a beam axis 1 perpendicular to the ground surface and in the above-stated order toward the ground. The range shifter 7 is disposed inside the vertical irradiation unit 6. The illustrated therapeutic apparatus also comprises a first image pick-up device including an X-ray CT (computed tomography) unit 11 connected to a computer 19 through a communication device 29, a data bus 28, and another communication device 27. The therapeutic apparatus of the illustrated embodiment further comprises a second image pick-up device including an X-ray tube 2, an X-ray tube controller 12, an image intensifier 13, an optical system 14, an auto-iris 15, a television camera 16 and a camera control unit 17. The above-listed members, except for the X-ray controller 12 connected to the X-ray tube 2 and the camera control unit 17 connected to the television camera 16, are aligned in the above-stated order, along the beam axis 1 toward the ground. The X-ray tube 2 is disposed between the dose monitor 8 and the collimator 9, and the collimator 9 is disposed between the X-ray tube 2 and the image intensifier 13. An analog-to-digital converter 18 is connected to the camera control unit 17. A computer 19 is connected to the analog-to-digital converter 18. A reference image display unit 20 and a pick-up image display unit 21 are connected to the computer 19. A character display unit 22, a keyboard 23 and an operation panel 24 are also connected to the computer 19. A tablet 25 is also connected to the computer 19 and is used an an input means. An image data file 26 is connected to the computer 19.

During positioning and during therapy, a therapy table 4 on which a patient 3 is laid in the supine position (with the face upward of "on his back") is disposed between the collimator 9 and the image intensifier 13. The therapy table 4 is provided with a built-in drive unit. The therapy table 4 is also connected to the computer 19.

The operation of the above-described therapeutic apparatus is now described with reference to FIG. 2, which shows the flow of operation of the therapeutic apparatus. The drawings (A) through (D) on the left show steps during therapy plannings. The drawings (E) through (H) on the right show steps during positioning.

During examination, X-ray CT images showing the location of the affected part of the patient picked up by an X-ray CT unit 11 are transmitted via the communication device 29, the data bus 28, the communication device 27 and the computer 19, to the image data file 26 and are accumulated in the image data file 26. As an alternative, the X-ray CT images may be recorded on a magnetic tape, a floppy disk or similar recording medium, and subsequently accumulated in the image data file 26.

Figure 2:
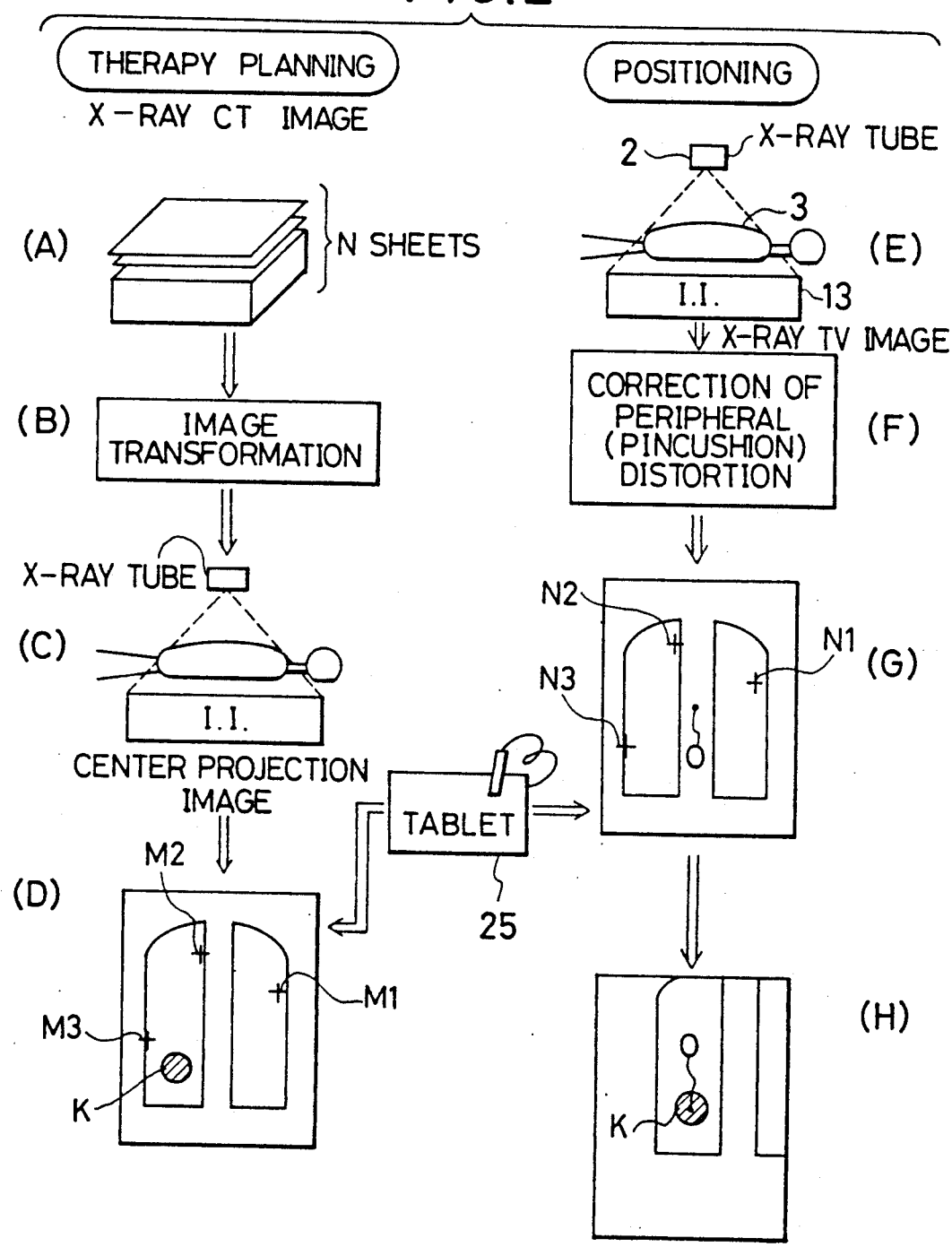
FIG. 2 is a schematic diagram showing the flow of operations of the therapeutic apparatus of FIG. 1.

During therapy planning, the X-ray CT images accumulated in the image data file 26 (schematically illustrated at (A) in FIG. 2) are converted (as shown by (B)) into a center projection image, an example of which is shown at (D) in FIG. 2. A center projection image is an image formed on a plane when X-rays radiating from a point (X-ray tube), are projected upon the patient, as shown in (C) in FIG. 2. The center projection image is displayed on the reference image display unit 20 as reference images. Using the tablet 25, three land marks Mi (i=1, 2, 3) are added to the reference images at locations of certain characteristic parts, such as bones, that can be identified on an image obtained by X-ray projection. The land marks Mi are used for indexing during positioning. In this connection, it should be noted that the affected part cannot be identified on an image obtained by X-ray projection. The computer 19 calculates the distances between the affected part K (indicated by hatching) and the land marks Mi. More than three land marks Mi may be used instead of just three, to increase the accuracy of the positioning.

During the positioning, a shown at (E) in FIG. 2, the patient 3 on the therapy table 4 is irradiated with an X-ray from the X-ray tube 2 having the voltage controlled by the X-ray controller 12. The X-ray images of the patient 3 of which the beam axis 1 can be identified are converted into optical images by the image intensifier 13. The optical images are then guided by the optical system 14, passed through the auto-iris 15, which automatically controls the iris of the television camera 16, and picked up by the television camera 16, thereby to be converted into electrical analog signals. The analog signals are converted by the analog-to-digital converter 18 into digital signals, which are then supplied to the computer 19. The computer 19 serves to perform signal processing. This signal processing includes correction or compensation for the periphery error (or pincushion distortion error). After the signal processing, the optical images are displayed on the pick-up image display unit 21. Land marks Ni (i=1, 2, 3) are appended to the X-ray TV image by input with the tablet 25. The computer 19 then calculates the distances between the center 0 of the beam axis 1 and the land marks Ni, and the distances between the affected part K and the center 0 of the beam axis 1. That is, as shown at (H) in FIG. 2, the distance that the therapy table 4 must move so that the affected part K coincides with the center 0 of the beam axis 1 is calculated. Moreover, the shape, dose and energy of the beam of the ionized particle beam are calculated by the reference image and the X-ray TV image. Control signals indicating the distance of the movement are supplied to the therapy table 4, which is thereby moved such that the ionized particle beam is accurately irradiated onto the affected part K.

During the actual therapy, the shape and depth of the affected part K, and the irradiated ionized particle beam absorption characteristic (absorption dose) are the parameters of the cancer therapy. On the basis of these, the ionized particle beam is controlled by the collimator 9, the range shifter 7, and the dose monitor 8, and irradiated onto the affected part K. More specifically, the ionized particle beam is reformed to have the shape coincident with the shape of the affected part K, and the energy of the ionized particle beam is varied through passage of a material with distributed (varied) energy absorption of the range shifter 7 and the range is thereby varied. The dose of irradiation of the ionized particle beam is monitored by use of the dose monitor 8. During such operation, the X-ray tube 2 is removed or retracted such that it does not interfere with the ionized particle beam.

Figure 3:
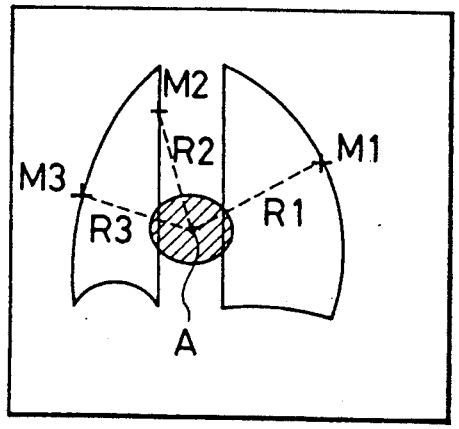
FIG. 3 shows the reference image on the X-Y plane at (A), and the corresponding X-ray TV image at (B).
Figure 3:
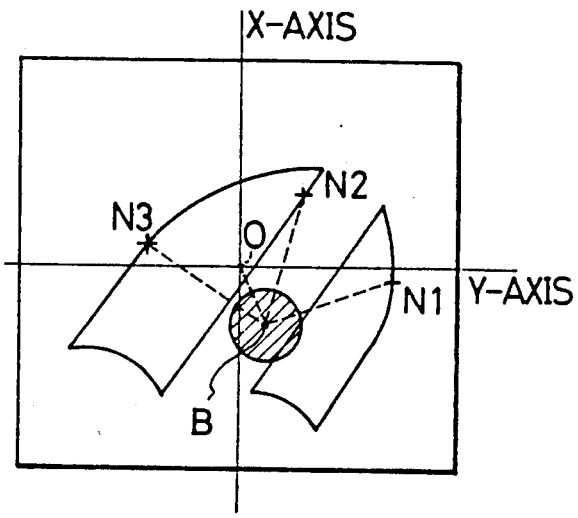
Figure 4:
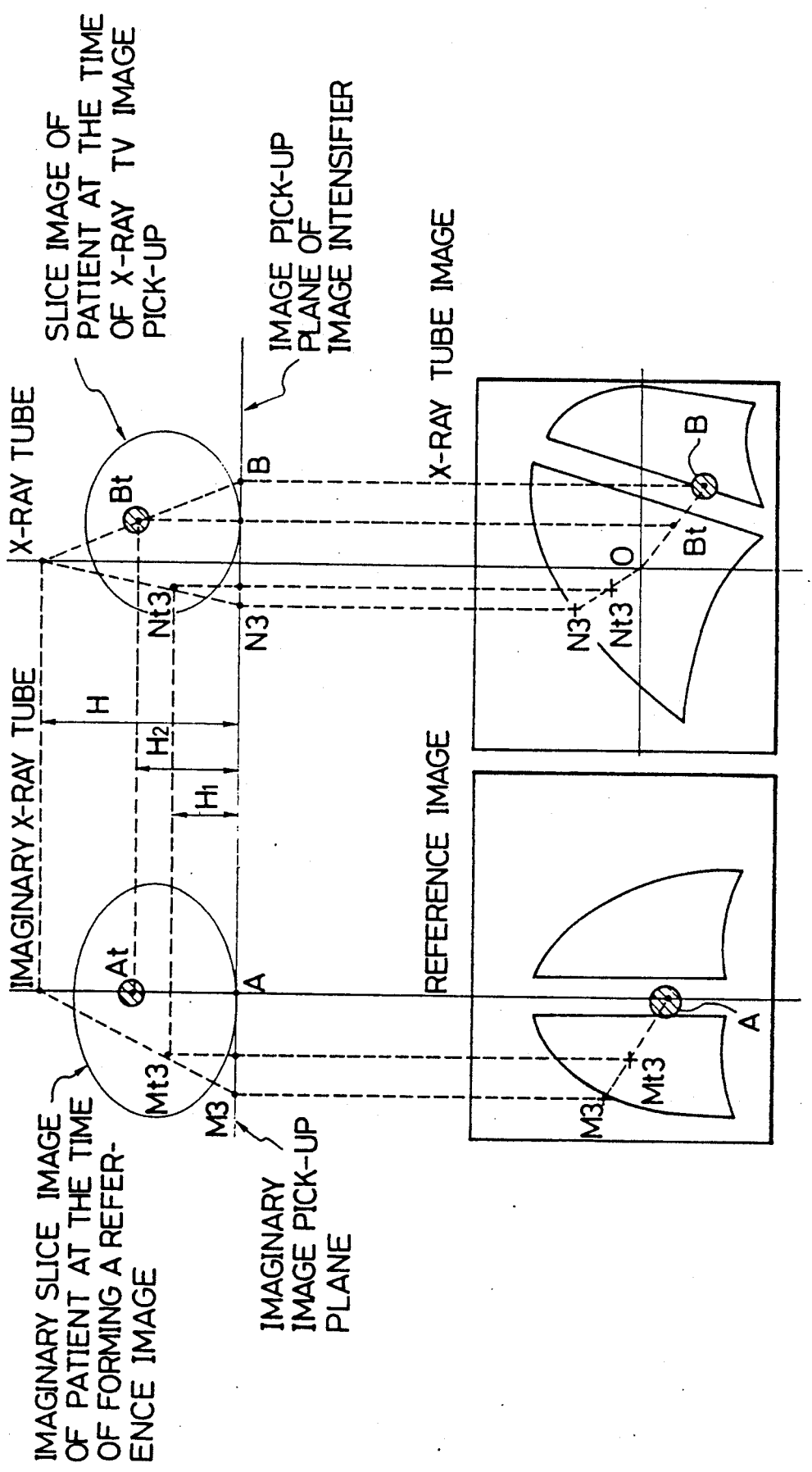
FIG. 4 is a diagram for explaining the relationship between the coordinate values and the true coordinate values on the X-Y plane.
Figure 5:
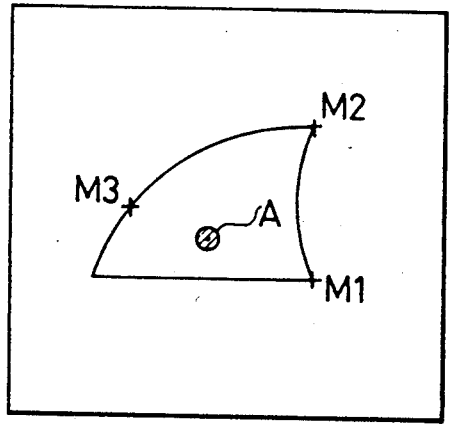
FIG. 5 shows the reference image on the Z-X plane at (A) and the corresponding X-ray TV image at (B).
Figure 5:
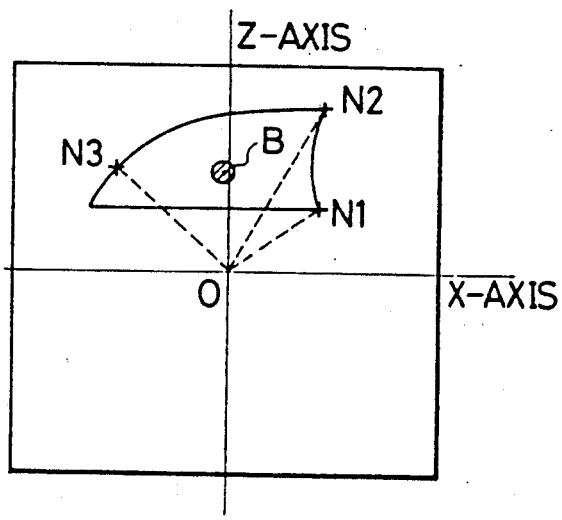

An embodiment of the invention is now described with reference to FIG. 3, FIG. 4, and FIG. 5. FIG. 3 shows the reference image on the X-Y plane at (A), and the corresponding X-ray TV image at (B). FIG. 4 is a diagram for explaining the relationship between the coordinate values and the true coordinate values on the X-Y plane. FIG. 5 shows the reference image on the Z-X plane at (A) and the corresponding X-ray TV image at (B).

The method of positioning by use of the X-ray TV image is as follows:

(1a) As shown if FIG. 3 at (A), the reference image is displayed on the reference image display unit 20. The hatched affected part K, the center A of the affected part K, the land marks Mi, and the distances Ri (i=1, 2, 3) from the center A of the affected part K to the land marks Mi are indicated.

(1b) As shown in FIG. 3 at (B), the X-ray image of the patient 3 is formed and displayed on the pick-up image display unit 21, after correction of the peripheral distortion of the digitized X-ray image. The X-ray TV image includes the profile of bones or the like (but the profile of the affected part K is not seen in the X-ray TV image), the center 0 of the beam axis 1, i.e., the center of X-ray TV image,) and X and Y axes. The center 0 of the beam axis 1 in the X-ray image is made to be at a position corresponding to the affected part K in the reference image.

(1c) As shown in FIG. 3 at (B), land marks Ni are appended to the X-ray TV image, by use of the tablet 25, at the positions corresponding to the land marks Mi on the reference image shown in FIG. 3 at (A). Apart from the image elements mentioned above, the affected part that is hatched, the estimated center B of the affected part, and the land marks Ni are also indicated in FIG. 3 at (B).

(1d) The distance of the movement of the therapy table 4 in a direction parallel to the X-Y plane is calculated. As shown in FIG. 3 at (B), the distance of the movement is represented by vector $\rightarrow OB$ (generally the vector from the coordinate P to the coordinate Q is represented by →PQ).

$$\rightarrow AMi = Ri \quad (1)$$

$$\rightarrow BNi = -\rightarrow OB + \rightarrow ONi \quad (2)$$

From the equation (2), $$\rightarrow OB = \rightarrow ONi - \rightarrow BNi \quad (3)$$

Since →BNi = →AMi = Ri $$\rightarrow OB = \rightarrow ONi - Ri$$

The values of →ONi start at the coordinate shown in FIG. 3 at (B).

(1e) The angle of rotation (rotational error) about the Z-axis of the therapy table 4 is calculated. In addition to the image elements shown in FIG. 3, the true center At of the affected part and the true land mark Mt3 are indicated in the reference image, and the true estimated center Bt of the affected part and the true land mark Nt3 are indicated in the X-ray TV image, as shown in FIG. 4. Moreover, the heights H, H1 and H2 of the X-ray tube 2, the true affected part center At (true estimated affected part center Bt) and the true land mark Mt3 (true land mark Nt3), with respect to the image pick-up plane of the patient 3 are also indicated.

First, the true affected part center Bt corresponding to the estimated affected part center B is calculated. Specifically, the true distances Rti (i=1, 2, 3) from the true land marks Nti (i=1, 2, 3) to the true affected part center Bt are calculated.

For example, as shown in FIG. 4, $$(\rightarrow ON3 - \rightarrow ONt3)/\rightarrow ON3 = H1/H \quad (4)$$

$$(\rightarrow OB - \rightarrow OBt)/\rightarrow OB = H2H \quad (5)$$

From the equations (4) and (5), the angle of rotation $\theta$ of the affected part is calculated by averaging the angle differences between the →AtMti (i=1, 2, 3) and →BtNti.

(1f) The therapy table 4 is moved by →OB in the X- and Y-axes and rotated by $\theta$ about the Z-axis. The positioning is thereby achieved.

In practice, the distance →OB of movement is displayed on the character display unit 22, on the basis of which the therapy table 4 is moved under manipulation by the operator (technical expert).

The positioning on the Z-X plane and/or Y-Z plane can be made in a manner similar to the above, if that is required.

(1g) As shown in FIG. 5, at (A) and (B), land marks Ni are appended in the X-ray TV image, at positions corresponding to the land marks Mi in the reference image, and the distance →OB of required movement in the Z-axis is calculated.

(1h) The therapy table 4 is moved by the distance of movement →OB in the Z-axis direction (up and down directions). The positioning is thereby achieved.

This completes the positioning by use of the X-ray TV image. When minute adjustment is required, the steps (1a) through (1h) can be repeated. The final confirmation is made by a doctor.

FIG. 6 shows another embodiment of the therapeutic apparatus according to the invention. This embodiment differs from therapeutic apparatus of the FIG. 1 in that the second image pick-up means is formed of an X-ray CT unit 13A, which is disposed on the beam axis 1, and the X-ray CT slice image picked up/obtained by the X-ray CT unit 13A is supplied to the computer 19.

Figure 6A:
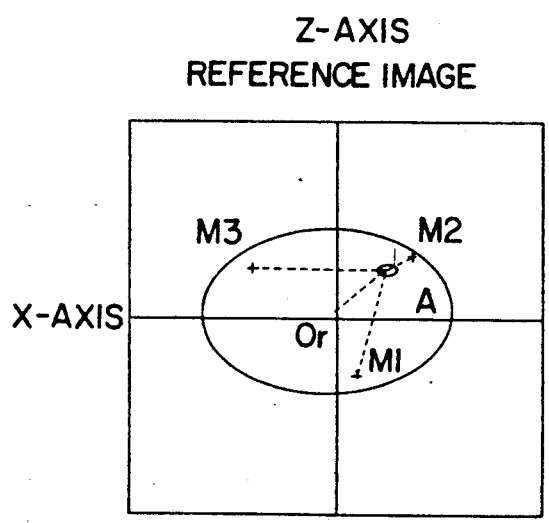
FIGS. 6A and 6B illustrate the reference image on the z-x plane and the corresponding X-ray CT slice image respectively, of the embodiment illustrated in FIG. 6.

The method of positioning by use of the X-ray CT images is described with reference of FIG. 6A and FIG. 6B. FIG. 6A shows the reference image on the Z-X plane and FIG. 6B shows the corresponding X-ray CT slice image.

(2a) As shown in FIG. 6A, the reference image is displayed on the reference image display unit 20. The reference image is obtained by appending land marks Mi, by use of the tablet 25, to slice image that has not been transformed into a center projection image. In FIG. 6A, the affected part is shown hatched, and the affected part center A, land marks Mi and the image center Or are indicated.

Figure 6B:
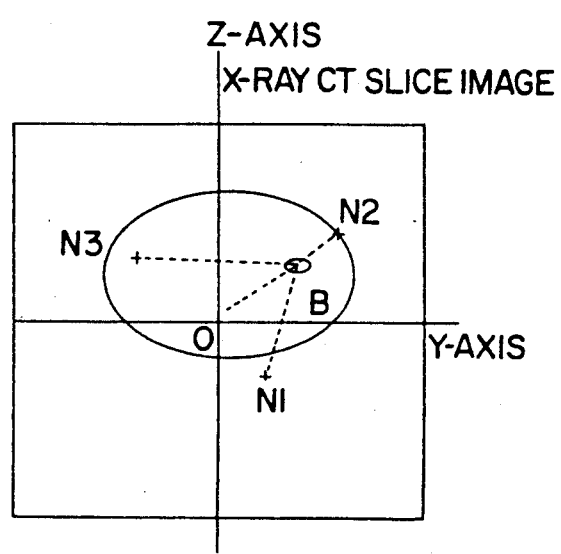

(2b) As shown in FIG. 6B, a plurality of slice images, including the affected part, are obtained by the X-ray CT unit 13A, and displayed on the pick-up image display unit 21. In FIG. 6B, the affected part is shown hatched, and the estimated affected part center B, land marks Ni and the image center (irradiation center) O, and Z- and Y-axes are indicated.

(2c) The X-ray CT slice images are successively displayed on the pick-up image display unit 21, and the X-ray CT slice image which coincides (most closely) with the reference image is selected by eye observation. From the number (representing the depth at which the X-ray CT slice image is taken) of the X-ray CT slice image that has been selected, the position along the X-axis of the affected part is determined.

(2d) Land marks Ni are appended, by use of the tablet 25, to the selected X-ray CT slice image at positions corresponding to the land marks Mi in the reference image. As a result, the affected part center B in the Z-Y plane is determined in the same manner as with the X-ray TV image.

(2e) The averages →MN of the vectors (deviations) →MiNi (i=1, 2, 3) of the land marks Mi and Ni with respect to the the image centers Or and O of the reference image and X-ray CT slice image, respectively, are calculated. The distances →OB of movement in the Z-Y axis directions of the therapy table 4 can thereby be determined. That is, the distance of the movement is given by:

$$\rightarrow OB = \rightarrow OrA + \rightarrow MN \quad (6)$$

(2f) The therapy table 4 is moved by the distance →OB in the Z-Y axis directions, and the positioning is thereby accomplished.

(2g) The therapy table 4 is moved by the necessary distance (as determined in the step (2c)) in the X axis direction, and the positioning is thereby accomplished.

This completes the positioning by use of the X-ray CT slice image. In this embodiment, becasue of the restriction against rotation of the therapy table 4 about the X axis, the rotational error cannot be corrected during the positioning in the Z-Y plane.

In this way, accurate positioning can be made in a simple manner and automatically. After the positioning the therapy using the ionized particle beam can be made in a manner known in the art, or in a manner described later in this specfication.

In the positioning using the X-ray TV images, the reference image and the center projection image are required. The X-ray TV image data (with land marks Mi) obtained by the processing at the time of therapy planning at the first occasion are transmitted to the computer 19, and can be used as the reference image in the subsequent occasion. This eliminates the transformation into the center projection image.

In the positioning using the X-ray CT slice images, the X-ray CT scanogram may be used as the reference image. In this case, a three-dimensional slice image can be obtained. The positioning in the X-Y plane can be made efficiently. However, with the X-ray CT scanogram, a measure may be required for correcting the image distortion due to the difference in the aperture of the X-ray CT unit.

Figure 7:
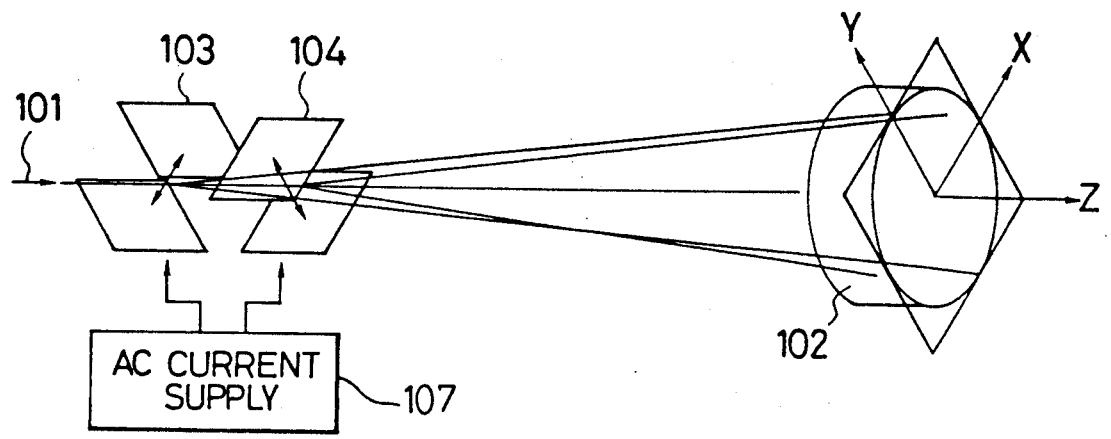
FIG. 7 is a schematic diagram showing an ionized particle beam apparatus which may be incorporated in the therapeutic apparatus shown in and described with reference to FIG. 1 to FIG. 6.
Figure 8:
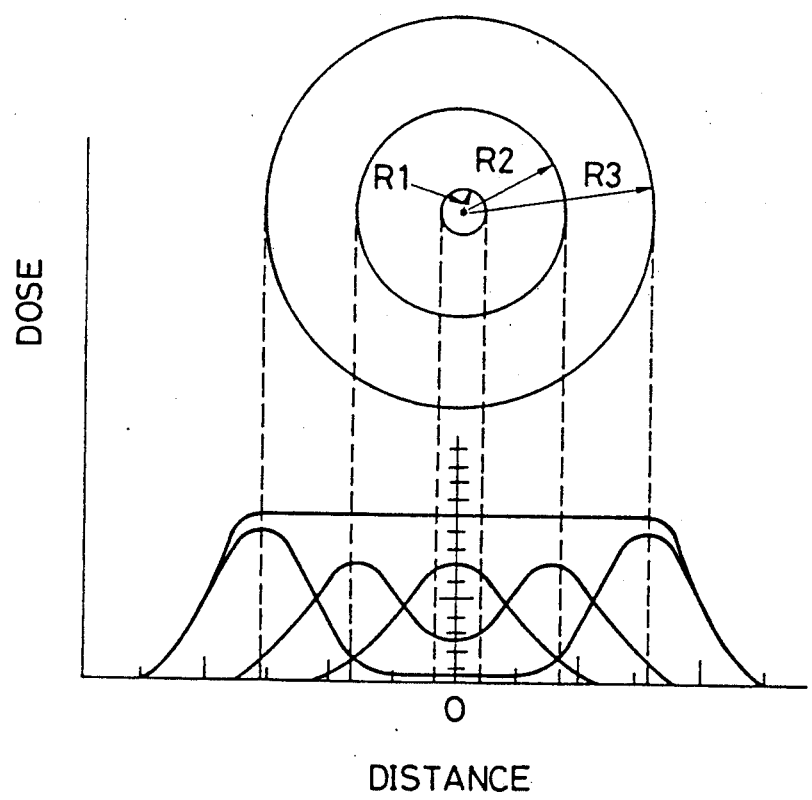
FIG. 8 is a diagram showing dose distribution when the ionized particle beam apparatus of FIG. 7 is employed.

FIG. 7 shows an example of an ionized particle beam apparatus for use in a therapeutic apparatus. As illustrated, it comprises an X-direction scanning electromagnet 103 and a Y-direction scanning electromagnet 104 disposed on the path of an ionized particle beam 101 from an ion source, not shown, to an affected part 102 which is in the irradiation field of the ionized particle beam. A current source 107 supplies AC currents 90° out of phase with each other to the X-direction scanning electromagnet 103 and the Y-direction scanning electromagnet 104 to generate a rotating magnetic field. By varying the strength of the electric currents to the respective electromagnets 103 and 104, the radius of the rotating magnetic field is varied, and the radius of the area on the plane of the affected part 102 irradiated with the ionized particle beam 101 is varied, as represented by R1, R2, R3 in FIG. 8. By combining the different radii of rotation, the dose distribution of the ionized particle beam 101 can be made uniform throughout the affected part 102.

Figure 9:
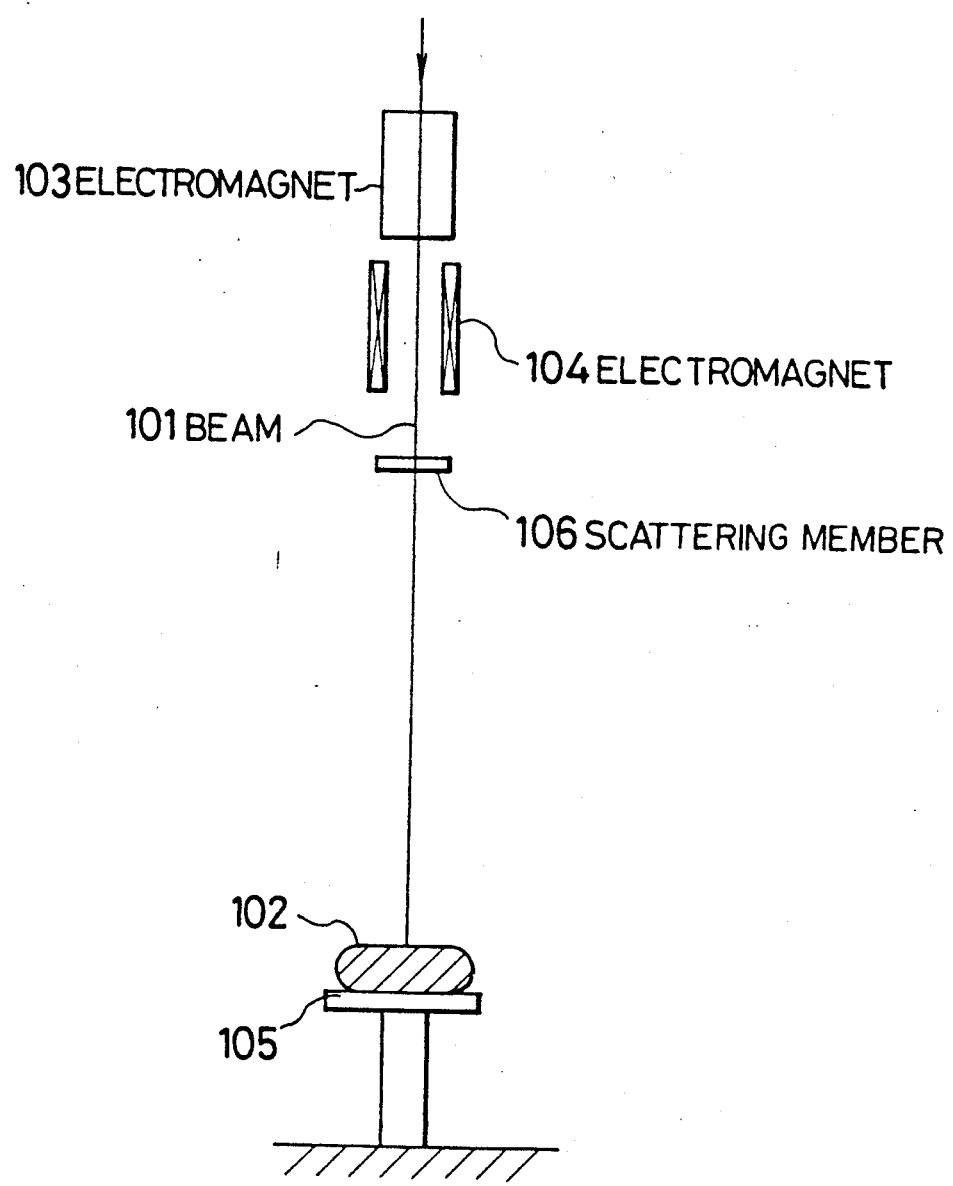
FIG. 9 is a diagram showing another embodiment of an ionized particle beam apparatus which may be incorporated in the therapeutic apparatus shown in and described with reference to FIG. 1 to FIG. 6.
Figure 10:
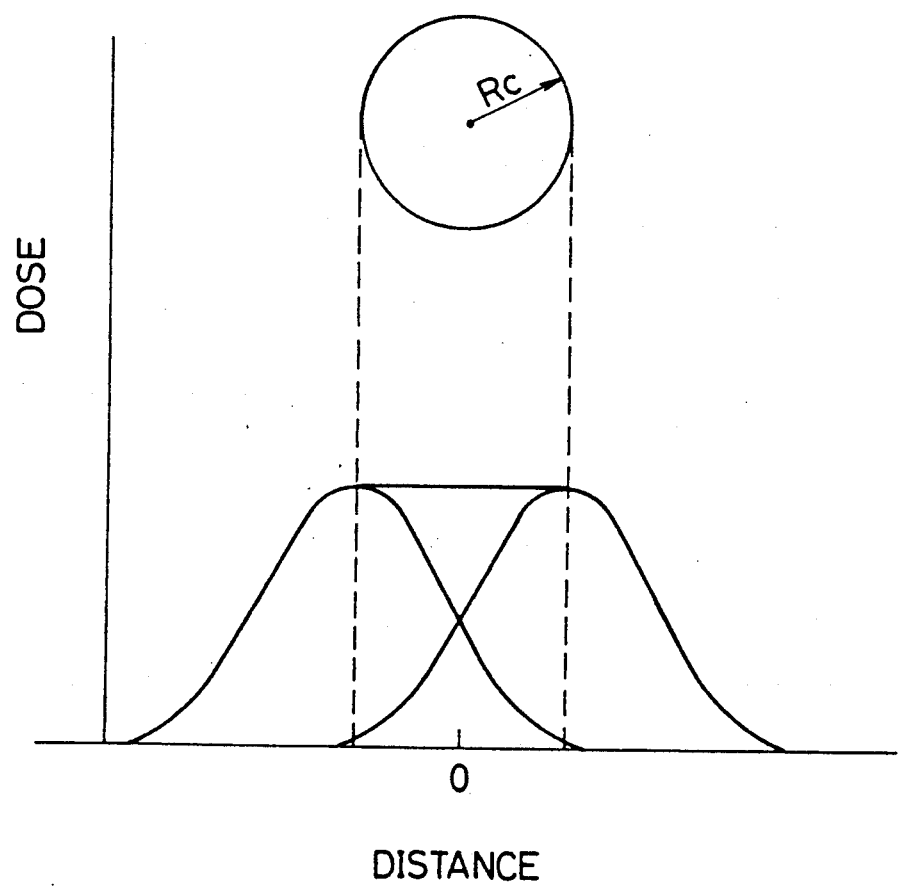
FIG. 10 is a diagram showing dose distribution when the ionized particle beam apparatus of FIG. 9 is employed.

Another example of the ionized particle beam apparatus for use in a therapeutic apparatus is shown in FIG. 9. The reference numerals identical to those in FIG. 7 denote identical or similar members or parts. A scattering member 106 is provided on the path of the ionized particle beam downstream of the X-direction scanning electromagnet 103 and the Y-direction scanning electromagnet 104. The scattering member 106 may, for example, be formed of a lead plate or a copper plate. The scattering member 106 serves to enlarge the radius of the ionized particle beam as irradiated onto the affected part 102 of the patient. When the ionized particle beam 101 passes through the scattering member 106, the particles of the ionized particle beam 101 are scattered in different directions. The amount of the particles of the ionized particle beam 101 directed to the respective directions form a normal distribution so that the radius of the ionized particle beam 101 is effectively enlarged. Thus by using an ionized particle beam 101 of a fixed rotation radius Rc, a uniform dose throughout the irradiation field can be obtained, as shown in FIG. 10.

In the embodiment described above, the scattering member 106 is disposed downstream of the scanning electromagnets 103 and 104, but it can alternatively be disposed upstream of the scanning electromagnets 103 and 104.

Figure 11:
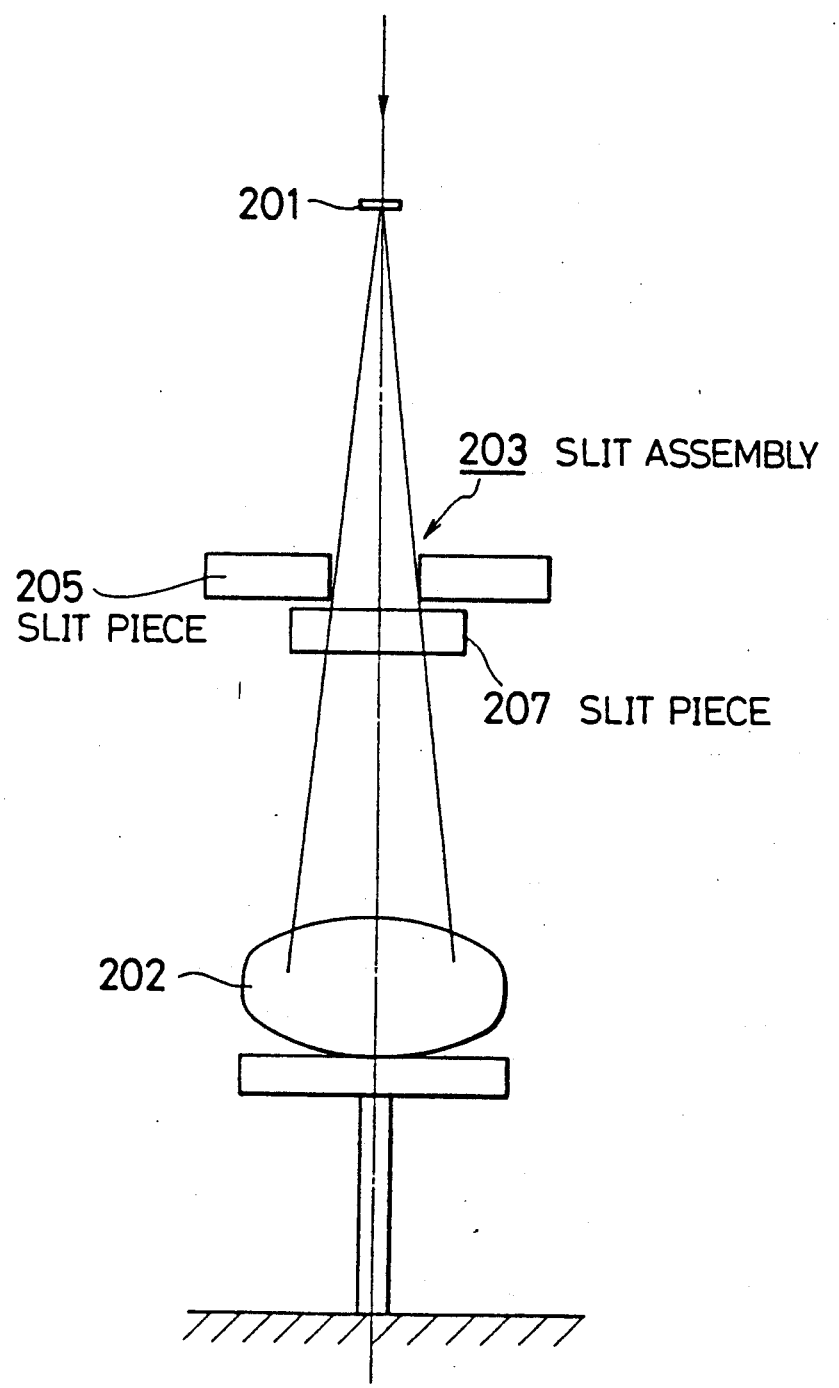
FIG. 11 shows how a slit assembly can be disposed in an ionized particle beam apparatus.

In order to restrict the profile of the ionized particle beam that is irradiated onto the affected part, a slit assembly may be used. FIG. 11 shows how a slit assembly can be disposed in an ionized particle beam apparatus. In the illustrated arrangement, the slit assembly 203 is disposed between a scattering member 201 and the affected part 202 which is an irradiated part. The slit assembly 203 serves to adjust the size of the ionized particle beam.

Figure 12:
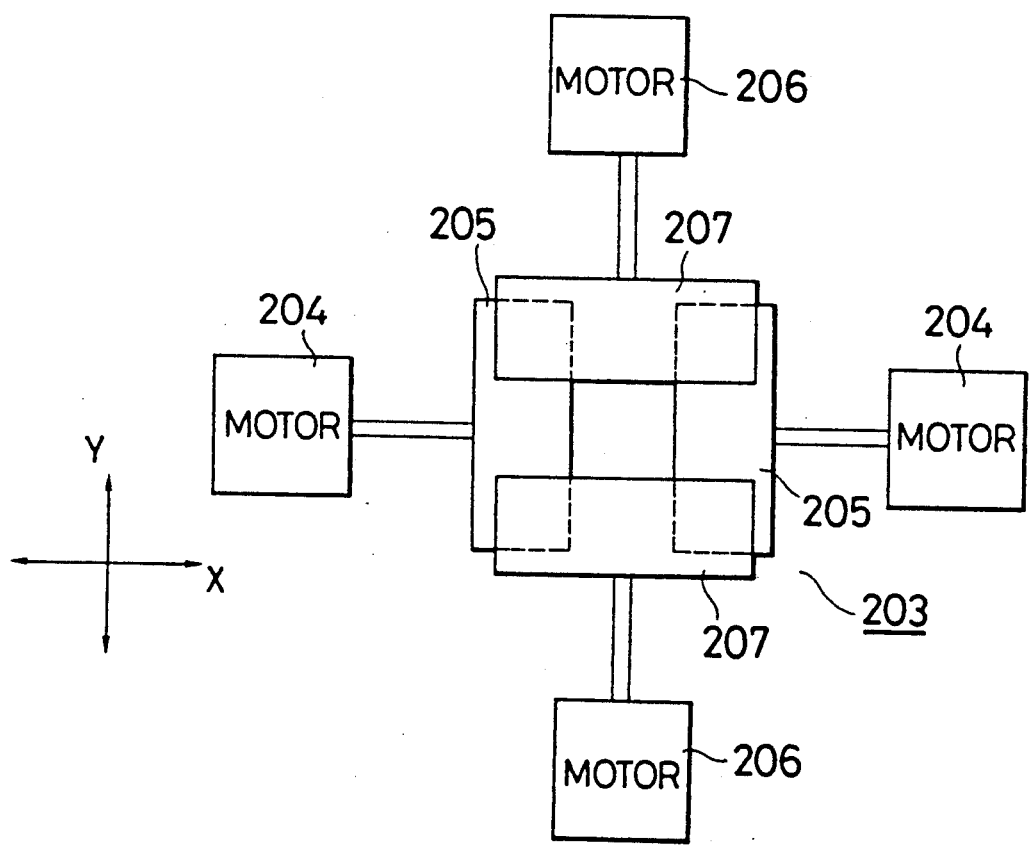
FIG. 12 shows an example of a slit assembly.

An example of the slit assembly 203 is shown in FIG. 12. As illustrated, it comprises a first pair of slit pieces 205 which are moved by a first motor 204 back and forth and toward and away from each other in the X-axis direction and a second pair of slit pieces 207 which are moved by a second motor 206 back and forth and toward and away from each other in the Y-axis direction. The ionized particles emitted from an electron gun, not shown, pass through the scattering member 201, which enlarges the diameter of the ionized particle beam. The ionized particle beam is however reduced in its diameter by an aperture defined by the inner edges of the slit pieces 205 and 207. When the slit pieces 205 and 207 are moved toward each other, the aperture is reduced. When the slit pieces 205 and 207 are moved away from each other, the aperture is enlarged. The ionized particle beam passing through the aperture is directed to the affected part 202.

Figure 13:
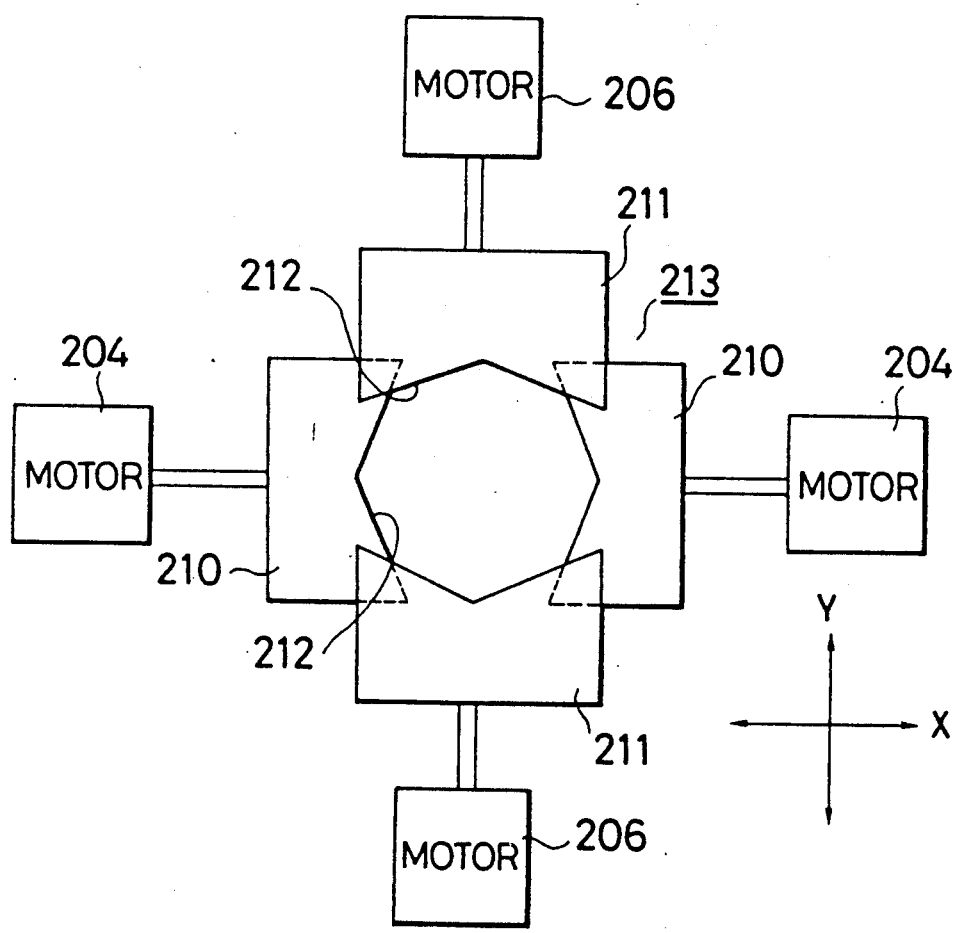
FIG. 13 shows another example of a slit assembly.

Another example of the slit assembly is shown in FIG. 13. As illustrated, it comprises a first pair of slit pieces 210 which are moved by a first motor 204 back and forth and toward and away from each other in the X-axis direction and a second pair of slit pieces 211 which are moved by a second motor 206 back and forth and toward and away from each other in the Y-axis direction. The aperture of the slit assembly through which the ionized particle beam passes is defined by the inner edges of the slit pieces 210 and 211. The inner edge of the slit pieces 210 and 211 are formed of two sides which are at an angle of about 135° relative to each other and which are symmetrical with respect to the line of the back-and-forth movement. As a result, the aperture defined by the inner edges of the four slit pieces 210 and 211 having two sides each is an octagon.

The ionized particles emitted from an electron gun, not shown, pass through the scattering member 201, which enlarges the diameter of the ionized particle beam. The ionized particle beam is however reduced in its diameter by an aperture defined by the inner edges of the slit pieces 210 and 211. When the slit pieces 210 and 211 are moved toward each other, the aperture is reduced. When the slit pieces 210 and 211 are moved away from each other, the aperture is enlarged. The ionized particle beam passing through the aperture is directed to the affected part 202.

The inner edge may have shapes other than that having the two sides as described above. For instance it may have such a shape that the aperture defined by the four slit pieces is, a 12-sided polygon, a 16-sided polygon, or the like. The shape of the aperture is desirably closer to a circle. The inner edge may have an other shape which is generally concave with respect to the center of the aperture.

The slit assembly shown in FIG. 13 has an advantage over the slit assembly shown in FIG. 12 in that it can effectively reduce the size of the beam. In the slit assembly shown in FIG. 12, the dimension from the center to the periphery of the aperture is not effectively reduced at the corners of the rectangular aperture defined by the slit pieces 205 and 207.

In the arrangement described above, the slit assembly is used in combination with a scattering member. But the slit assembly may alternatively be used in combination with a pair of deflecting (or scanning) electromagnets deflecting the beam in directions orthogonal to each other.

During irradiation with an ionized particle beam onto the affected part, it is desirable to measure the dose and/or the location of the irradiation. An apparatus shown in FIG. 14 has been devised to enable this. In FIG. 14, an ionized particle beam (e.g., a heavy particle beam) 301 with a high energy is irradiated onto an affected part of a patient 303 for the purpose of cancer therapy. The affected part is identified by an X-ray CT unit or the like and the therapy table 302 is moved so that the affected part aligns with the ionized particle beam 301. The dose of irradiation and the depth of irradiation are determined in advance according to the therapy plan. A plurality of Γ-ray detectors 304 are disposed around the affected part. When the ionized particle beam 301 is irradiated onto the patient 303, it looses its energy in the tissues within the body 303. An example of the absorption dose of the ionized particle beam 301 is shown in FIG. 15. The abscissa indicates the irradiation depth and the ordinate indicates the dose (intensity). In the case of heavy particle beam (beam of particles having a mass greater than a proton) in particular, the absorption dose at the irradiation corresponding to the irradiation energy is the greatest. This property can be utilized to concentrate the radiation on the affected part.

When the ionized particle beam 301 irradiated inside the body of patient 303 is transformed, with a certain probability, the cells inside the body or the irradiated particles themselves are transformed into positron emitting nucleuses. The positron emitting nuclide includes $^{19}Ne$, $^{15}O$ $^{11}C$. The positron emitting nucleuses emit positrons which are united with electrons and are therefore annihilated to produce radiant energy. At the time of the annihilation two photons of 511 KeV corresponding to the rest energy of the electron are emitted in opposite directions. When the photons are received by the Γ-ray detectors 304 they produce output signals. A calculating means 305 receives the outputs of the detectors 304 and calculates the locations at which the photons are emitted and accumulates the result of such calculations to measure the dose at the respective locations. In this way, the information on the location where the ionized particle beam 301 is actually irradiated and the information on the irradiation dose can be obtained.

In the above example, the kinds of the heavy particle beams are identified. But by directly irradiating the positron emitting nuclide, the information on the location is obtained more effectively.

The Γ-ray detectors 304 opposite to each other may be combined to form a pair. Moreover, the time difference between the receipt of the two photons at the Γ-ray detectors 304 may be determined to identify the location of the positron emitting nuclide where the positron is generated.

It is also desirable to confirm the configuration of the irradiation field by use of a light field localizer. An example of the arrangement of light field localizer is shown in FIG. 16. In FIG. 16. reference numeral 401 denotes an ionized particle beam, 402 is a scattering member, 403 is a light field localizer, 403a is a light source, 403b is a reflecting mirror, 404 is the affected part, and 405 is a collimating slit.

An ionized particle beam 401 accelerated to a high energy by an accelerator not shown is expanded by the scattering member 402. The scattering angle is thereby enlarged, and uniform irradiation over a wide area of the affected part is enabled. The configuration of the irradiation field is confirmed by the light field localizer 403. It is necessary that the distance between the light source and the irradiated surface of the patient is equal to the distance between the scattering member and the irradiated surface. When illuminated by the light field localizer, the reflecting mirror is moved onto the central axis of the beam such that it is as if the light were emitted from the scattering member. The configuration of the affected part is known in advance from an X-ray photograph or X-ray CT apparatus.

With the above arrangement, since the distance between the light source and the irradiated surface of the patient must be equal to the distance between the scattering member and the irradiated surface, the light source of the light field localizer must be positioned far from the patient. Where various devices have to be disposed between the scattering member and the patient, it is difficult to confirm the configuration of the irradiation.

Another example of the arrangement of the light field localizer shown in FIG. 17 has been devised to solve this problem and to enable disposition of the light source of the light field localizer close to the patient.

In FIG. 17, the reference numerals identical to those in FIG. 16 denote identical or similar members or parts.

In the example of FIG. 17, the ionized particle beam 401 is rotated by X- and Y-direction scanning electromagnets so that the dose distribution is made uniform. By the action of a range shifter 407 the energy of the ionized particle beam 401 can be attenuated. The depth of the irradiation can thereby be adjusted according to the depth of the affected part. The uniformity and the dose rate of the beam can be measured by a beam monitor 408. When various devices are disposed between the scanning electromagnets and the patient as illustrated, it is preferable that the light localizer be disposed near the patient. For this reason, it is necessary that the distance between the light source and the patient be shorter than the position at which the actual beam is expanded (i.e., the position of the scanning electromagnets, in the example under consideration). For this reason, a lens system 403c is disposed between the light source 403a and the patient, so that the same effect is obtained as if the light is emitted from the position of the scanning electromagnets. The reflecting mirror is retracted during the confirmation of the irradiation configuration.

Figure 18A:
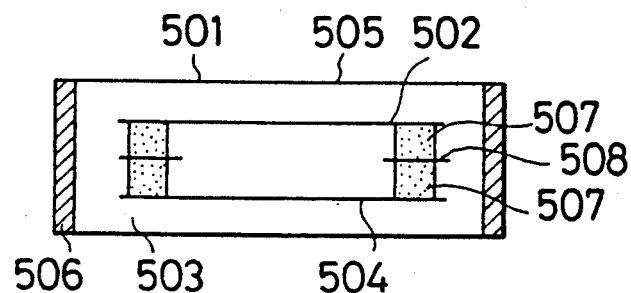
FIG. 18A is a side view showing a particle beam monitor device.
Figure 18B:
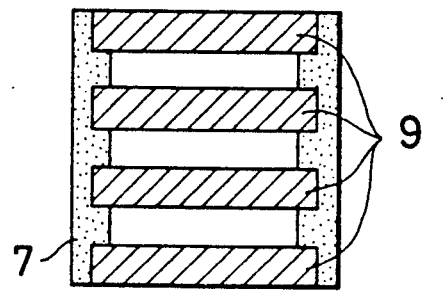
FIG. 18B is a diagram showing the uniformity measurement electrodes.
Figure 18C:
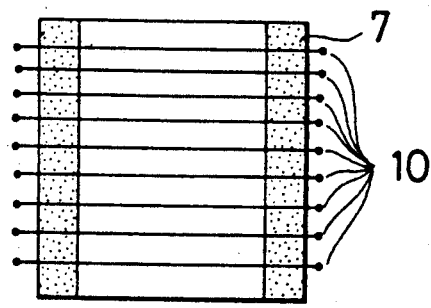
FIG. 18C is a diagram showing the profile measurement electrodes.

It is also desirable to provide a particle beam monitor device. FIG. 18A, FIG. 18B and FIG. 18C show an example of particle beam monitor device 501. It comprises a housing 506 in which gas 503 is sealed, a particle beam-transparent plate permitting passage of a particle beam while maintaining the seal, and a collector electrode 502 for collecting electrons and ions generated by ionization of the gas 503 due to the particle beam passing through the monitor device 501.

Figure 20:
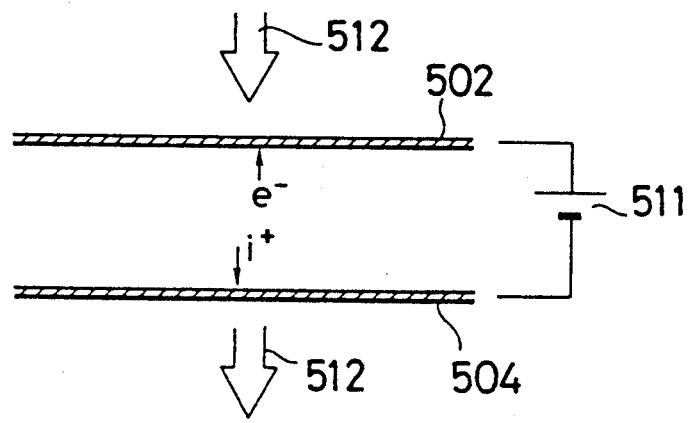
FIG. 20 shows how a high-voltage power supply is connected to the particle beam monitor device.

A high-voltage electrode 504 is provided to energize the ionized electrons and ions. As shown in FIG. 20, a high-voltage power supply 511 is connected across the high-voltage electrode 504 and the collector electrode 502. An insulating plate 507 insulates the collector electrode 502 and the high-voltage electrode 504. A guard electrode 508 prevents leakage current (from the high-voltage electrode) flowing through the surface of the insulating plate 507 from reaching the collector electrode 502. The guard electrode 508 is set at the same potential as the collector electrode 502.

The collector electrode 502 may be in the form of a dose measurement electrode (not shown) for measuring the particle beam dose over the entire surface, a uniformity measurement electrode 509, e.g., a set of small-sized electrodes disposed equi-distant from each other as shown in FIG. 18B, for measuring the intensity distribution of the particle beam over the predefined extension, or a profile electrode 510 consisting of wire-shaped electrodes as shown in FIG. 18C, for measuring the profile of the particle beam.

The collector electrodes 502 are made of a metal film, e.g., aluminum film, of 0.2 mm thick. The electrons $e^-$ collected by the collector electrodes are transferred through the leads (not shown), and an amplifier to an instrument for measurement, which are not shown.

Figure 19:
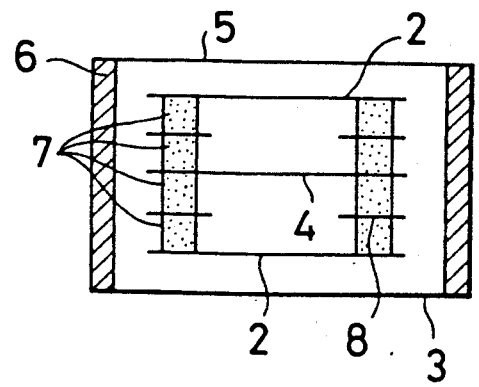
FIG. 19 is a side view showing another example of a particle beam monitor device.

FIG. 19 shows another example of a particle beam monitor device. In this example, one of the collector electrodes 502 is a dose measurement electrode and the other collector electrode 502 is a uniformity measurement electrode 509.

When a particle beam 512 passes through the gas 503 in the monitor device 501, the particle beam 512 collides with the gas molecules and the gas 503 is thereby ionized. The ionized electrons $e^-$ are collected to the collector electrode 502 and the ions $i^+$ are collected to the high-voltage electrode 504. The number of electrons $e^-$ and the ions $i^+$ is in proportion with the intensity of the particle beam 512. Since electrons move much faster than the ions, it is common to make the detection at the electron collector electrode for the monitoring of the passing particle beam 512.

Since the collector electrode 502 is formed of metal films of a thickness on the order of 0.2 mm, when the monitor device is used for the measurement of an X-ray or electron beam, the energy loss due to interference between the incident ion particle beam and the atoms of the metal film is not considerable. However, in the case a of heavy ion particle beam, the energy loss is not negligible and the monitor device is not suitable for accurate measurement. Moreover, the uniformily (flatness) measurement electrodes cannot make the measurement on the same plane, and has to make the measurement on different planes for the two axes. This also degrades the accuracy of the measurement.

Figure 21:
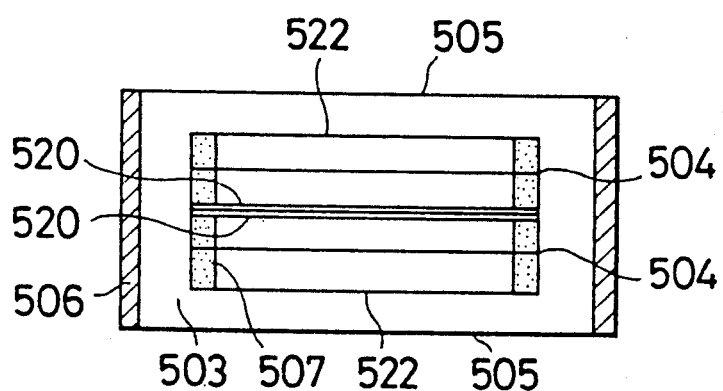
FIG. 21 shows another example of a particle beam monitor device.
Figure 22:
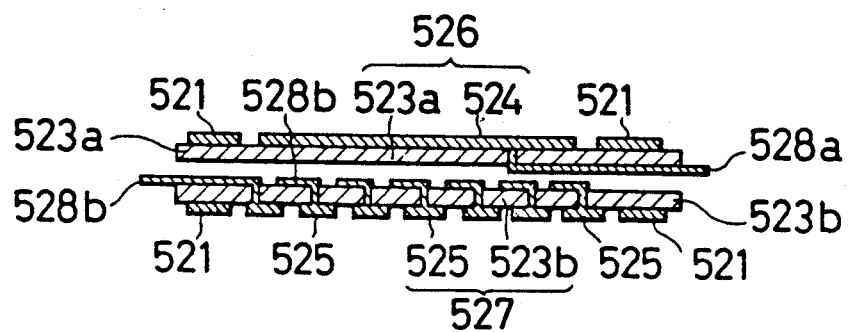
FIG. 22 is an enlarged diagram showing the collector electrode in FIG. 21.
Figure 23:
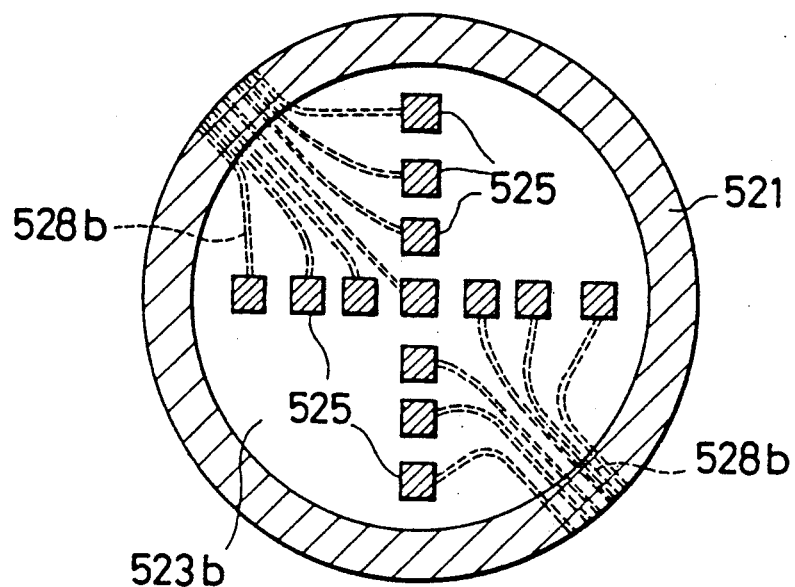
FIG. 23 is a bottom view of the device shown in FIG. 22.

Another example of the monitor device shown in FIG. 21, FIG. 22 and FIG. 23 has been devised to solve these problems. The reference numerals identical to those in FIG. 18A to FIG. 18C, FIG. 19 and FIG. 20 denote identical or similar members or parts. A collector electrode 520 is formed of metal film adhered or deposited by evaporation or plating onto a resin plate having a small specific gravity. An auxiliary electrode 522 is disposed to cancel the electrostatic force to the high-voltage electrode 504. It is disposed opposite the high-voltage electrode 504 to the rear surface of the high-voltage electrode 504 with, the high-voltage electrode 504 being disposed opposite the collector electrode 520 with the intervening insulating plate 507 interposed therebetween.

The collector electrode 520 comprises two resin plates 523a, 523b, such as polyimide resin plates, the rear surfaces of which are juxtaposed. More specifically, a disk shaped metal film 524 or annular metal films 524 are adhered, by evaporation or plating, on a surface of one resin plates 23a to form dose measurement electrode 526, and metals films 525 including a multiplicity of pieces arranged radially and adhered, by evaporation or plating, on a surface of the other resin plate 23b to form uniformity measurement electrode 527 (see FIG. 23). The uniformity measurement electrode 527 is so formed to enable the uniformity measurement on the same surface. Leads 528a for the dose measurement electrode 526 and leads 528b for the uniformity measurement electrode 527 are led out to and extend on the rear surfaces of the resin plates 523a, 523b in such a manner that they are not in contact with each other.

When a particle beam 512 passes through the housing 506 filled with a gas 503, the particle beam 512 and the molecules of the gas 503 collide with each other and the gas molecules are ionized. If a strong electric field is applied between the high-voltage electrode 504 and the collector electrode 520, the ionized electrons $e^-$ are collected to the collector electrode 520 and the ions $i^+$ are collected to the high-voltage electrode. The number of the ionized electrons and the ions is proportional to the strength of the passing particle beam 512. Since the moving speed of the electrons $e^-$ is higher than the moving speed of the ions $i^+$, the electrons $e^-$ are collected by the collector electrodes 520 and this is measured by a measurement circuit (not shown). That is, the irradiation dose is measured by the dose measurement electrode 526, and the distribution of the strength of the particle beam, when it is expanded and distributed, by the uniformity measurement electrode 527.

Figure 24:
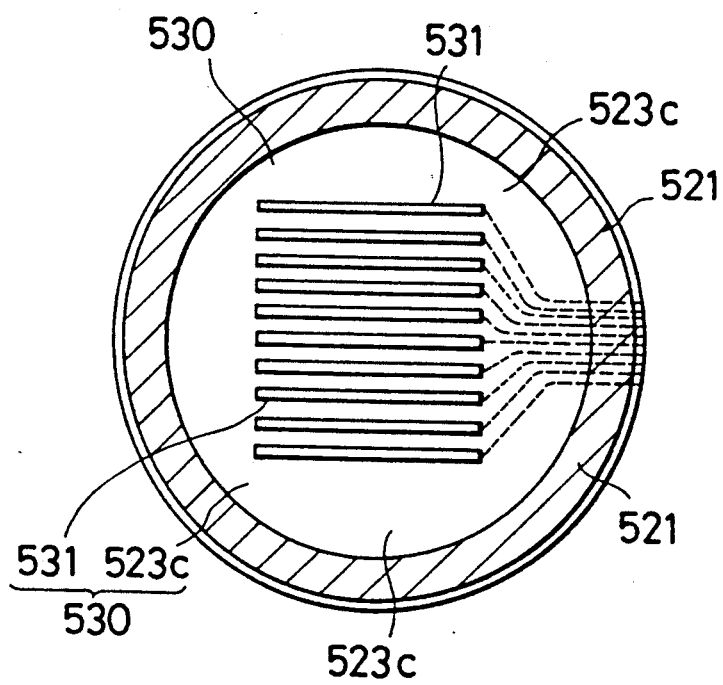
FIG. 24 is a plan view showing another example of a particle beam monitor device.

In the above example, the collector electrodes are a dose measurement electrode and a uniformity measurement electrode. But one of the collector electrodes may be a profile measurement electrode, as shown in FIG. 24, for measurement of the profile of the particle beam. That is, a multiplicity of horizontally extending linear metal films 531 are adhered, by evaporation or plating, on one of the resin plates, such as polyimide plate 523c of which rear surfaces are juxtaposed, and a multiplicity of vertically extending linear metal films are adhered, by evaporation or plating, on the other resin plate 523c.

The configuration of the electrodes for the dose measurement, the uniformity measurement and for the profile measurement, are not limited to those described, but can be modified in various ways.

As has been described, if the collector electrode is formed by adhering metal, by evaporation or plating, on a resin plate, the energy loss of the particle beam is reduced and accurate measurement can be attained. Moreover, if the rear surfaces of the two collector electrodes are juxtaposed, no static electric power is applied to the collector electrode. The location and the shape of the electrode can be determined accurately. The accuracy of the measurement is thereby improved. Moreover, the size of the apparatus can be reduced.

Another example of range adjuster will now be described.

Figure 25:
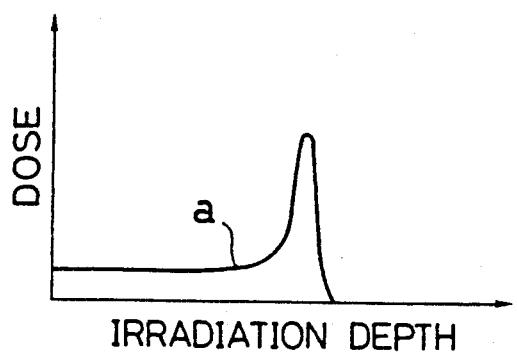
FIG. 25 is diagram showing the dose distribution in relation to the irradiation depth (range).
Figure 26:
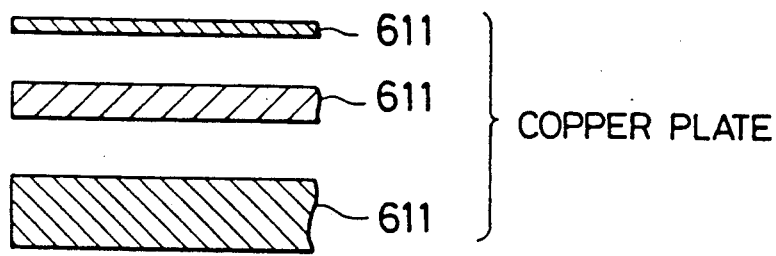
FIG. 26 is a cross sectional view showing an example of a range adjuster.

The dose distribution or profile when a high-energy proton beam or heavy ion beam is irradiated within the body is as shown in FIG. 25 by a curve (a). As shown, the peak is present at a position close to the range of the irradiation depth. Because of this nature, a high-energy proton beam and a heavy ion beam are utilized for killing cancer cells inside the body. With this method, the normal cells near the surface of the body are not damaged but the cancer cells are effectively killed. Moreover, where the cancer cells extend over a wide range, the irradiation energy can be successively changed to successively change the range. As a simple means for changing the irradiation energy, a range adjuster consisting of an energy absorption member is inserted in the path of the beam. The range adjuster may comprise one or more copper plates 611, shown in FIG. 26, stacked upon each other. The thickness may vary from one copper plate to another. The number of stacked copper plates 611 may be changed and copper plates of differing thicknesses may be chosen to adjust the total absorption.

Figure 27:
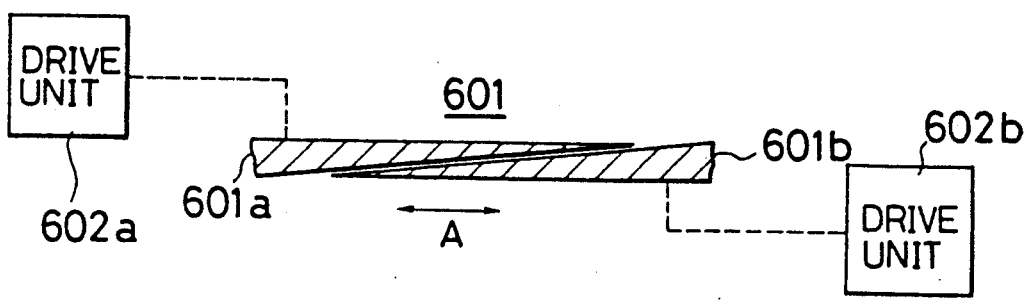
FIG. 27 is a schematic side view of another example of a range adjuster.

Another example of a range adjuster is shown in FIG. 27. This range adjuster comprises a pair of wedge-shaped energy absorption members 601a and 601b of copper or the like which are superimposed with each other and disposed in such a manner that the directions in which the wedge-shaped members 601a and 601b are tapered are opposite each other, and drive units 602a and 602b which drive the wedge-shaped members 601a and 601b back and forth in the directions in which the wedge-shaped members are tapered. The total thickness of the wedge-shaped members 601a and 601b through which the beam must pass can be continuously varied by moving the wedge-shaped members 601a, 601b in the directions of arrow A in which they are tapered. The range adjuster shown in FIG. 27 is advantageous in that it requires only a pair of wedge-shaped members and permits continuous adjustment of the range.

In performing ionized particle beam therapy, it is desirable to conduct three-dimensional irradiation in conformity with the shape of the affected part. An arrangement for this purpose will now be described with reference to FIG. 28 to FIG. 33.

Figure 28:
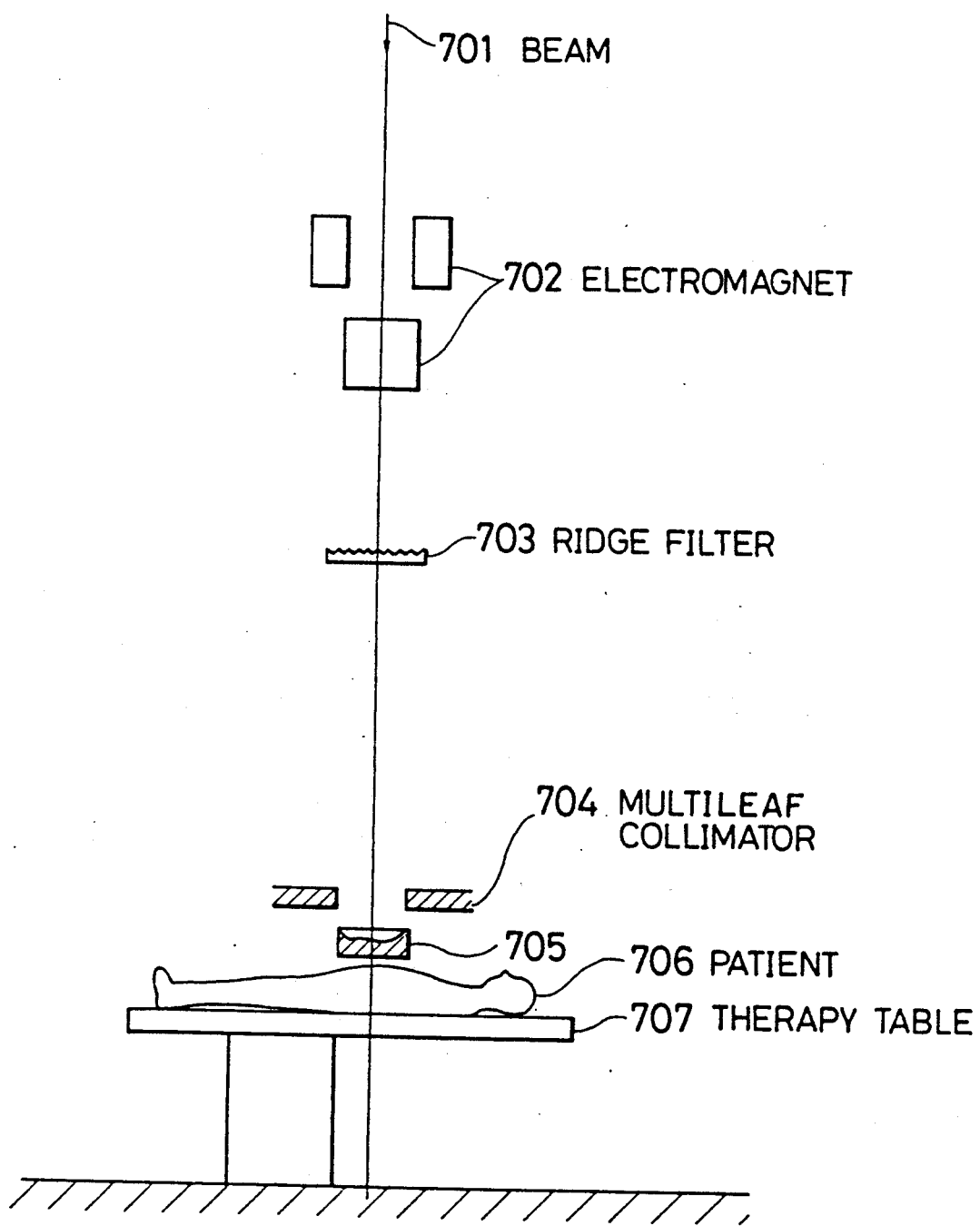
FIG. 28 is an elevational view of another embodiment of an ionized particle beam cancer therapy apparatus.
Figure 29:
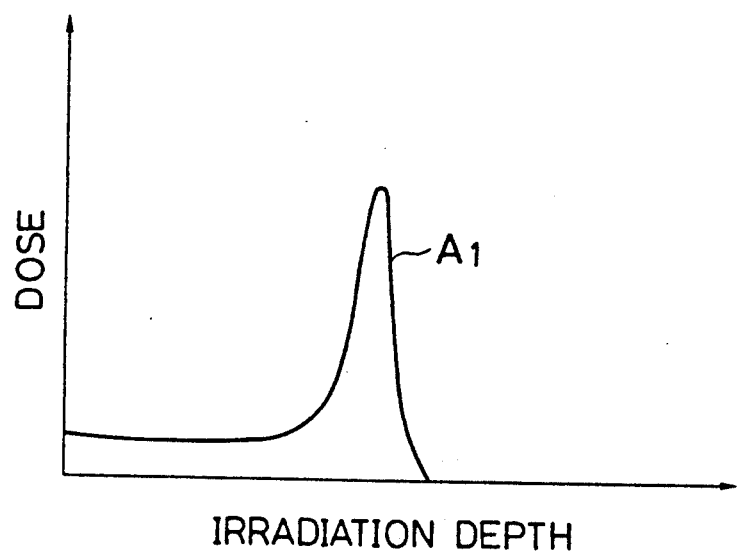
FIG. 29 is a characteristic diagram showing the absorption dose of the ionized particle beam.
Figure 30:
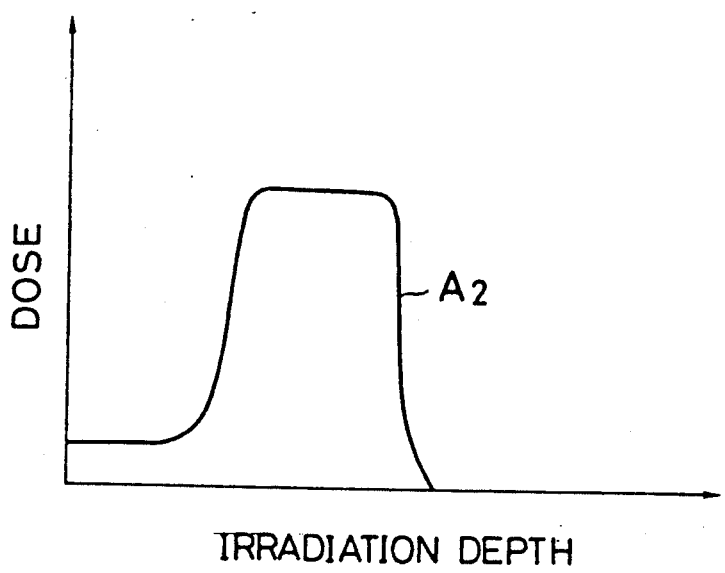
FIG. 30 is a characteristic diagram showing another example of an absorption dose of the ionized particle beam.
Figure 31:
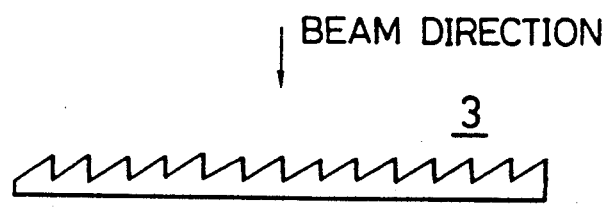
FIG. 31 is a cross sectional view of a ridge filter.
Figure 32A:
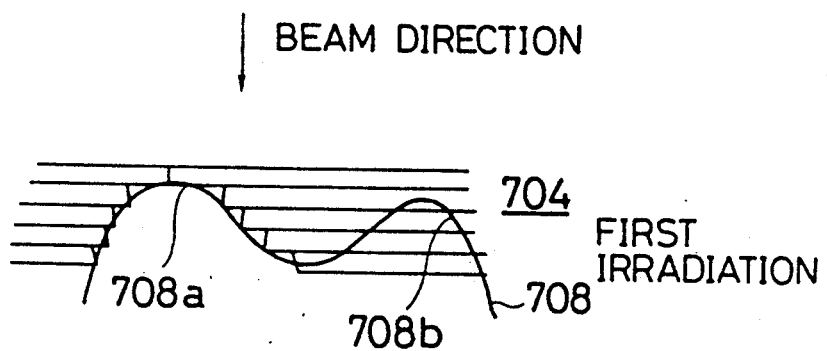
FIG. 32A and FIG. 32B are schematic diagrams showing the operation of a multileaf (multiple-leaf) collimator
Figure 32B:
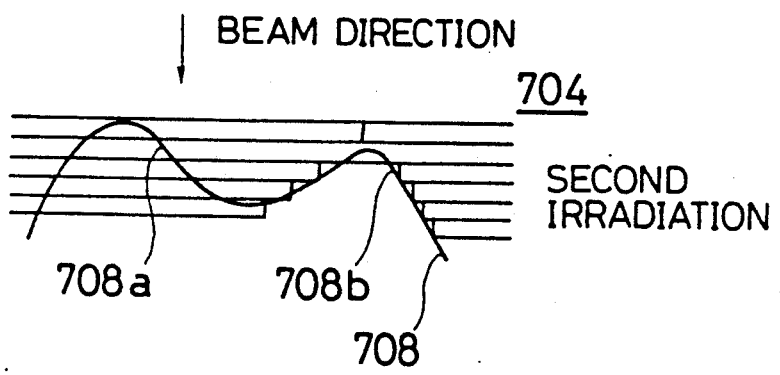
Figure 33:
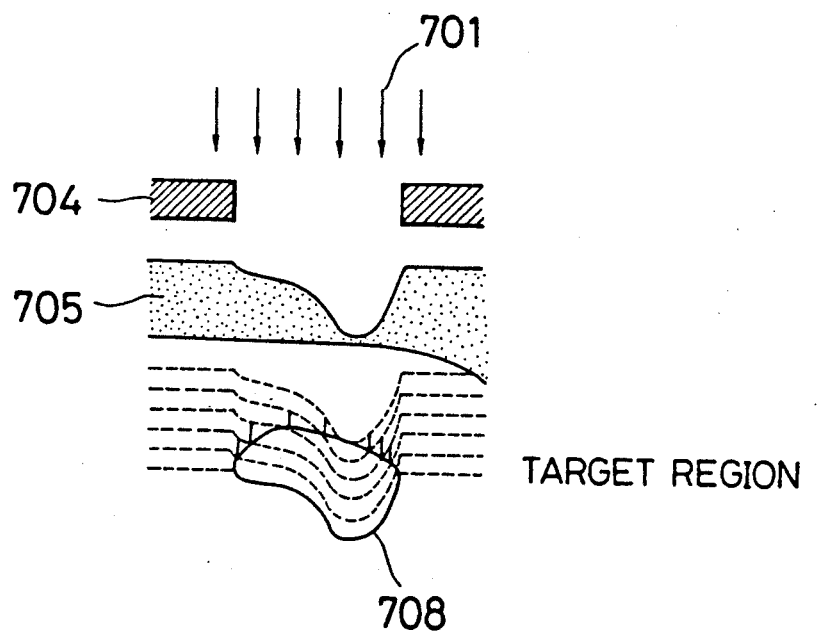
FIG. 33 is a schematic diagram showing the operation of the bolus.

In FIG. 28, an ionized particle beam 701 accelerated to a high energy by an accelerator, not shown, is circularly scanned by two scanning electromagnets 702, the magnetic fields of which are perpendicular to each other so that the beam dose distribution is uniform over the affected part. The dose distribution or profile of the ionized particle beam 701 along the depth of the irradiation is such that it has a peak at a certain depth, as indicated by curve A1 in FIG. 29. This property can be utilized to irradiate a maximum dose at the affected part at any given depth within the body of the patient 706. When the affected part extends in the depth direction more than the width of the irradiation peak, a ridge filter 703 can be used to obtain a dose distribution having a flat peak extending a certain distance in the depth direction, as shown by curve A2 in FIG. 30. The cross section of the ridge filter 703 has many protrusions, as shown in FIG. 31. The beam enters from the top as seen in the figure, and as indicated by an arrow, and the dose distribution in the depth direction is extended for the height of the protrusions (difference in thickness between the protruded parts and the non-protruded parts). A multileaf collimator 704 restricts the shape of the beam within the plane normal to the beam path into conformity with the shape of the affected part. That is, as shown in FIG. 32, corresponding to the first and second beam irradiations that are performed with some time interval therebetween, collimator pieces are moved, and the beam shape can be successively conformed with the two protrusions 708a, 708b. The bolus 705 is provided to conform the beam shape with the shape of the affected part in the depth direction (direction in which the beam proceeds). As shown in FIG. 33, the bolus 705 has convexes and concaves in the direction of the beam 701 so that the depth of the irradiation is changed depending on the local thickness as shown by a broken line.

A drawback associated with the above described arrangement is that a ridge filter and a bolus have to be provided for the individual patients.

Figure 34:
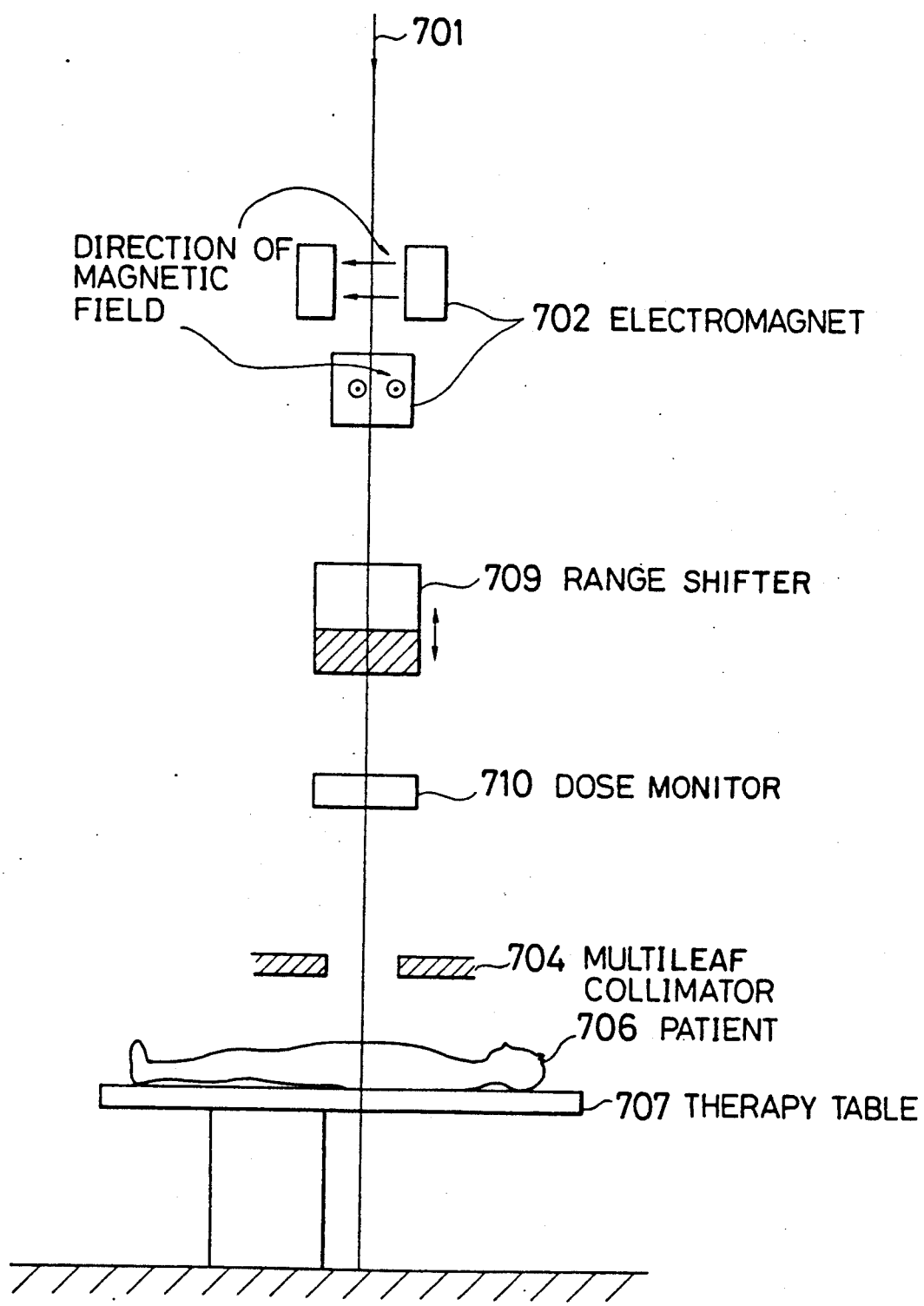
FIG. 34 is a schematic elevational view showing another embodiment of an ionized particle beam cancer therapeutic apparatus.

Another example of arrangement for conducting the three-dimensional irradiation for eliminating the above drawback is shown in FIG. 34.

In FIG. 34, the reference numerals identical to those in FIG. 28 denote identical or similar members or parts as in FIG. 28. Additional components are a range shifter 709 and a dose monitor (or dose meter) 710 which are disposed along the path of the ionized particle beam 701.

The ionized particle beam 701 which has been made uniform over a circular area by scanning electromagnets 702 passes through the range shifter 709 by which the energy of the ionized particle beam 701 is changed. The range shifter 709 comprises water, brine or some other liquid, or a plurality of plates of copper or the like. The energy of the ionized particle beam 701 is degraded in proportion to the thickness of the range shifter 709 which the ionized particle beam 701 must pass. Thus the irradiation energy can be varied without varying the energy of the accelerator. It is desirable that the thickness of the energy degrader of the range shifter 709 can be changed continuously so that the energy of the ionized particle beam 701 can be changed depending on the depth of the affected part.

A multileaf collimator 704 is used to define the irradiation field in the direction perpendicular to the beam axis. The multileaf collimator 704 has a function by which one of each pair of leaves, of plural pairs of leaves, can cover the irradiation field of the other leaf as well. In the illustrated arrangement under consideration, the range shifter 709 and the multileaf collimator 704 are combined to conduct the three-dimensional irradiation in conformity with the shape of the affected part. This allows maximum efficiency of the radiation therapy. That is, the range shifter 709 can be used to adjust the irradiation position in the direction of the depth and the multileaf collimator 704 can be used to vary the shape of the irradiation in the plane perpendicular to the beam axis.

The procedure for three-dimensional irradiation will now be described with reference to FIG. 35 to FIG. 38.

Figure 35:
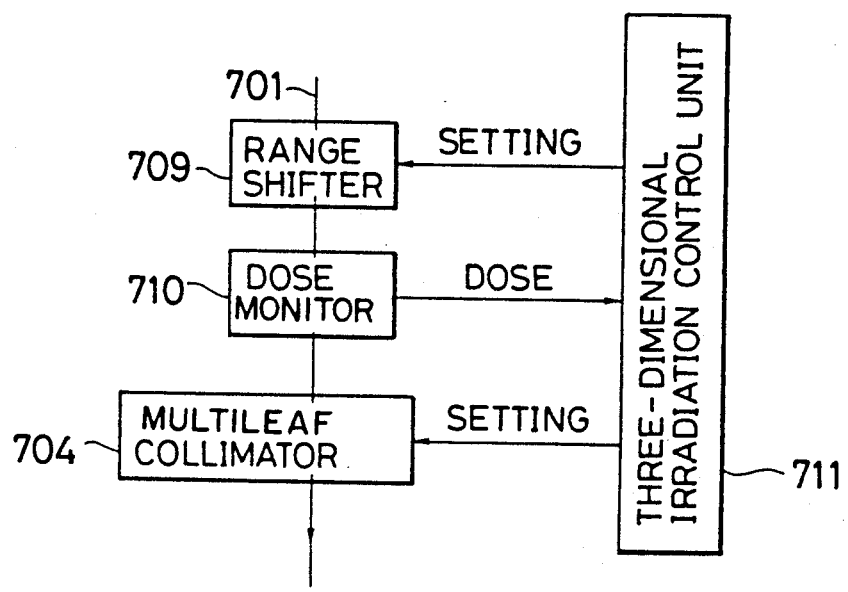
FIG. 35 is a schematic diagram showing the operation of the range shifter and the multileaf collimator.

FIG. 35 shows how a three-dimensional irradiation control unit 711 is connected to the range shifter 709, the dose monitor (dose meter) 710, and the multileaf collimator 704. The three-dimensional irradiation control unit 711 receives the dose signal from the dose monitor 710 and provides control signals by which the operating conditions of the range shifter 709 and the multileaf collimator 704 are set.

Figure 36:
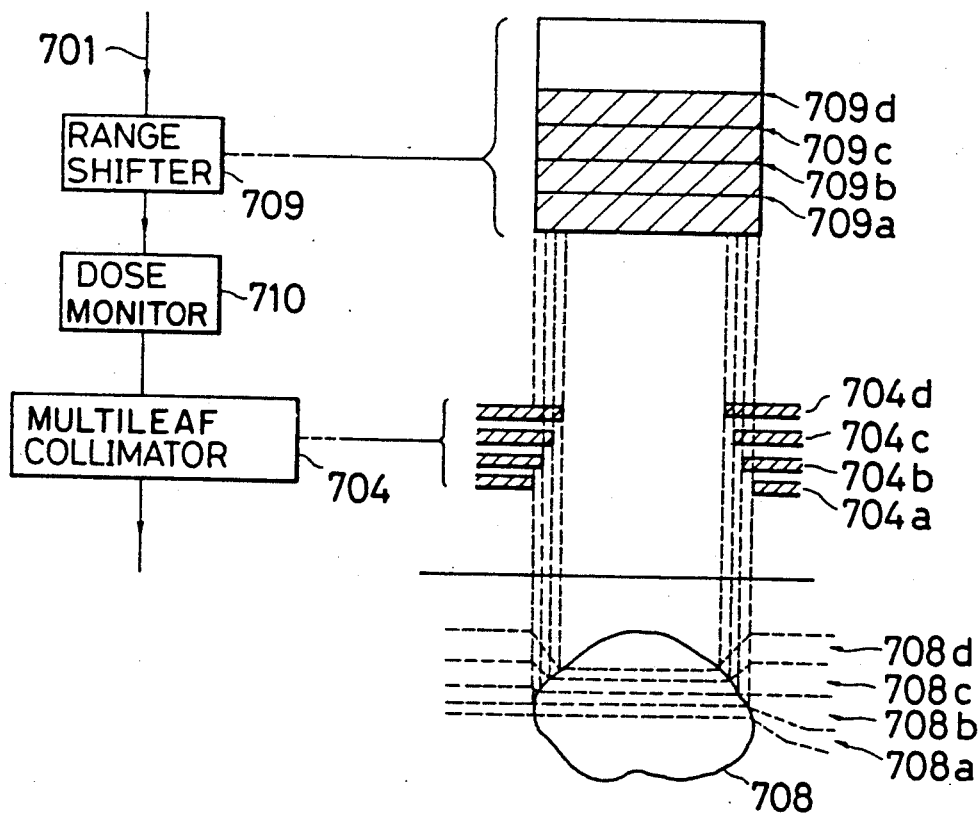
FIG. 36 is a schematic diagram showing the operation of the range shifter and the multileaf collimator corresponding to the respective layers of the affected part.
Figure 37:
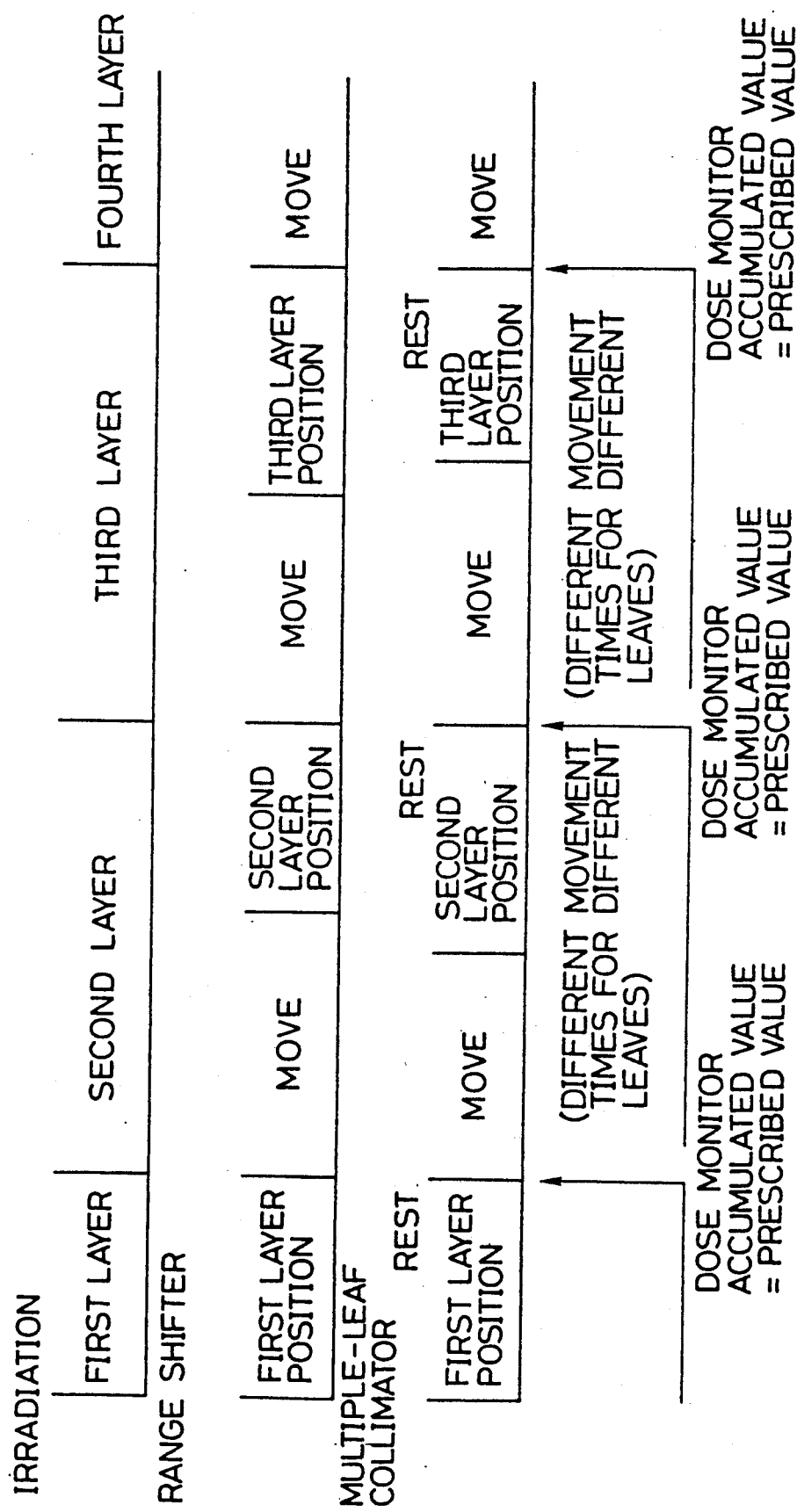
FIG. 37 shows the progress, with time, of the above operations.

FIG. 36 shows the operation of the range shifter 709 and the multileaf collimator 704 corresponding to the respective layers of the affected part 708. Reference numerals 708a, 708b, 708c, and 708d denote first to fourth layers of the affected part 708. 704a, 704b, 704c and 704d are positions of the multileaf collimator 704 at the time of irradiating the first to fourth layers 708a to 708d, respectively. 709a, 709b, 709c and 709d are positions of the range shifter 709 at the time of irradiating the first to fourth layers 708a to 708d, respectively. FIG. 37 shows the progress with time of the above operation. As shown the range shifter 709 and the multileaf collimator 704 are moved and stopped to control the dose.

Figure 38:
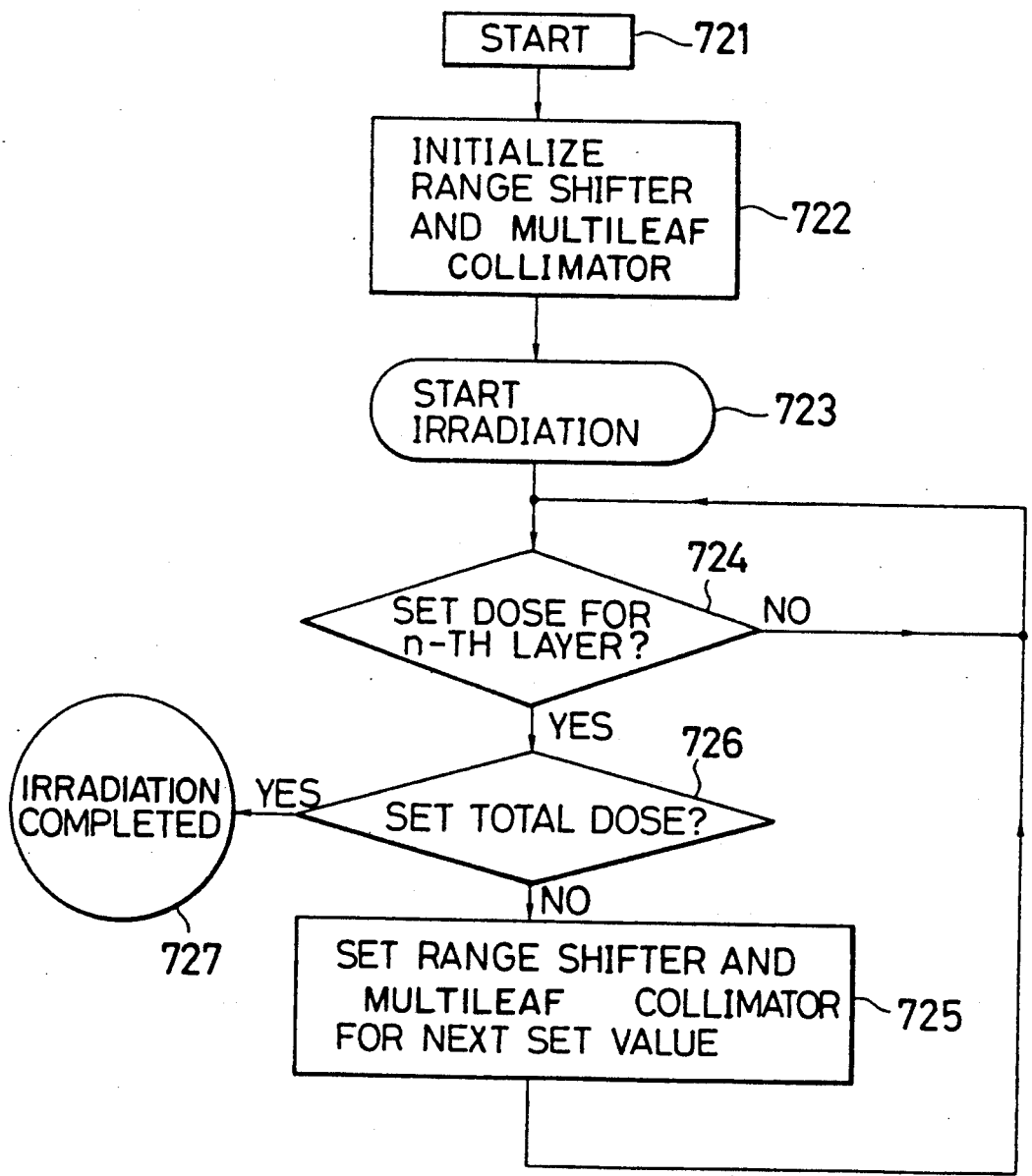
FIG. 38 is a flow chart showing the operation of the irradiation.

FIG. 38 shows a sequence of three-dimensional irradiation. First, a starter 721 is used to set the initial operating conditions of the range shifter 709 and the multileaf collimator 704 (722), and the irradiation is then started (723). When the irradiation of the set dose (724)

for the n-th layer is completed, the range shifter 709 and the multileaf collimator 704 are set for the next set value on the basis of the signal from the dose monitor 710, and irradiation for the next layer is conducted. This process is repeated for the respective layers. When the set total irradiation is reached for all the layers (726), the irradiation is completed (727).

In this way a uniform three-dimensional irradiation field is formed.

In the example described above, the range shifter 709 and the multileaf collimator 704 are combined. But the ridge filter and the bolus, described with reference to FIG. 28, can also be combined.

When the affected part has two protrusions in the direction of the beam, as shown in FIG. 32, a superimposed irradiation can be conducted, in which the three-dimensional irradiation is conducted for one of the protrusions, and then for the other protrusion.

Figure 39:
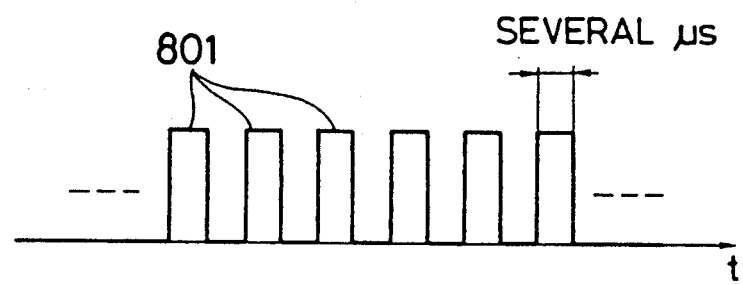
FIG. 39 is a time chart showing a series of beam pulses.
Figure 40:
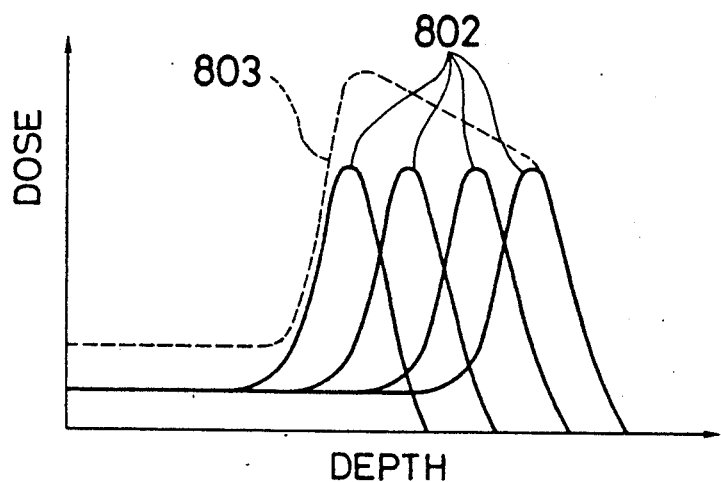
FIG. 40 is a graph showing the dose distribution with respect to the depth in the body when the dose of irradiation for different depths is not changed.
Figure 41:
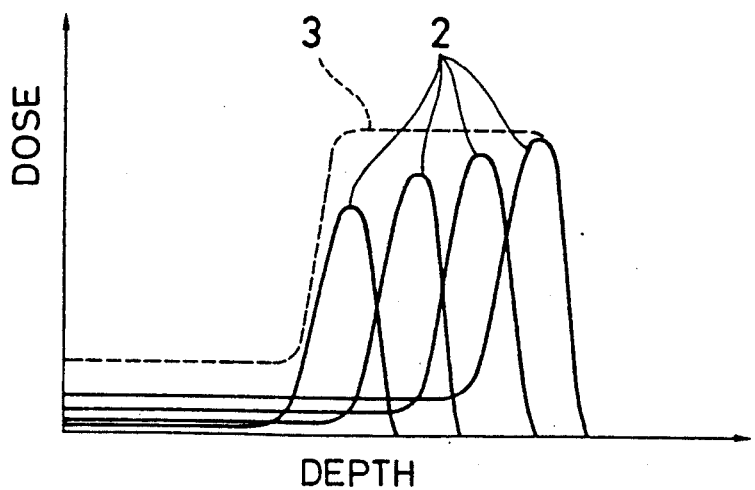
FIG. 41 is a graph showing the dose distribution with respect to the depth in the body when the dose of irradiation for different depths is adjusted.

Irradiation can be made by a series of beam pulses and the number of pulses can be changed to adjust the irradiation dose. The series of beam pulses 801 are shown in FIG. 39. The duration of each pulse can be several λm. Use of shorter duration permits finer adjustment of the dose. To change the depth of irradiation, it is desirable that the energy of the beam be changed between successive beam pulses. Each pulse 801 has an identical dose. The dose is detected by a dose monitor and is used to control the pulse 801. As illustrated in FIG. 25, although the irradiation dose curve has a peak at a certain depth, which varies depending on the energy of the beam, there is a part of substantially constant dose in the portion shallower than the position of the peak. If the pulses 801 of the same dose are irradiated for different depths (i.e., with different energies), the total does will be greater in the shallower part because the substantially constant part of the dose curves are added in the shallower part. The resultant total dose will be as indicated by curve 803 in FIG. 40. To compensate for this, the irradiation for the shallower part of the affected part is made with a smaller dose, as shown in FIG. 41. If for instance the irradiation is started with the deepest part of the affected portion and the depth of the irradiation is successively made shallower, the irradiation done is successively made smaller. The amount by which the irradiation dose is made smaller for the irradiation of the shallower part is determined so that the irradiation dose is uniform throughout the entire depth of the affected part.

Figure 42:
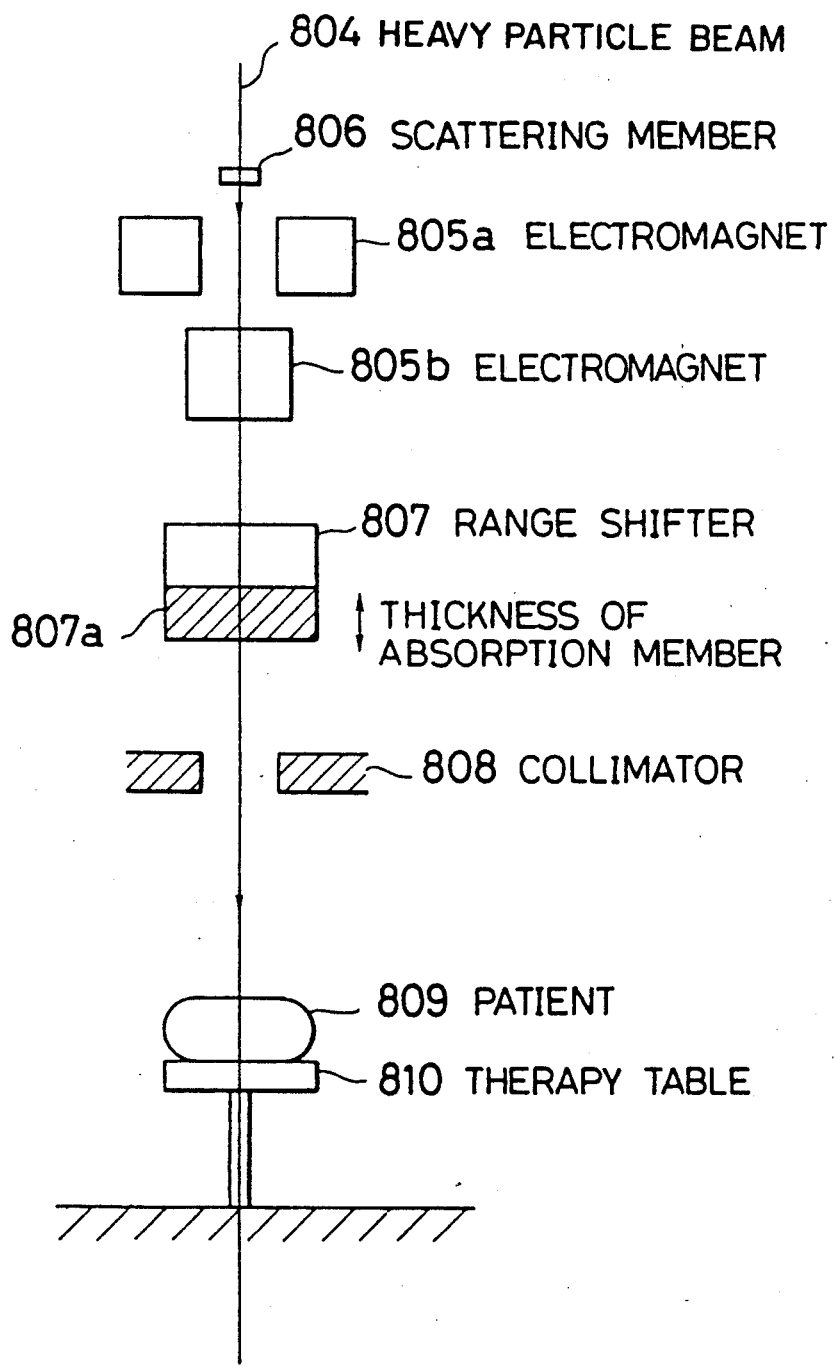
FIG. 42 is a schematic diagram of another embodiment of an ionized particle beam therapeutic apparatus.

An example of an apparatus used for implementing the above method is shown in FIG. 42. An ionized particle beam 804 is a heavy particle beam of an atomic nucleus heavier than a proton. A scattering member 806, scanning electromagnets 805a and 805b, a range shifter 807 having an absorption member 807a with variable thickness, and a collimator 808 are disposed on the path of the beam 804. The patient 809 is shown lying on a therapy table 810.

The beam 804 is circularly scanned by the scanning electromagnets 805a and 805b so that uniform dose distribution is achieved on the patient 809. The scattering member 806 is used to enlarge the diameter of the beam 804 so that the dose distribution uniformly is attained in a wider area.

Figure 43:
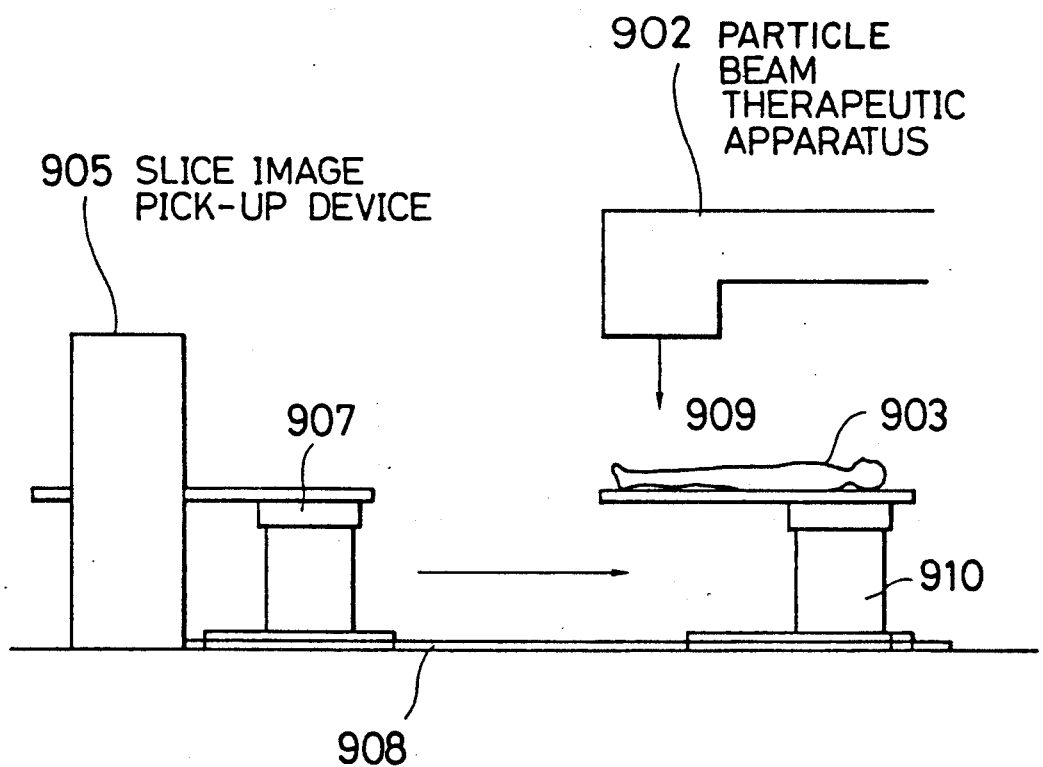
FIG. 43 is an elevational view showing a therapy and diagnosis system including a therapy/diagnosis bed.

A therapy bed suitable for use with the particle beam therapeutic apparatus will now be described with reference to FIG. 43. Reference numeral 902 denotes a particle beam therapeutic apparatus, and 905 is a slice image pick-up device or nuclear magnetic resonance slice image pick-up device. 907 is a therapy/diagnosis bed on which a patient 903 is laid. The therapy bed 907 has rollers, not shown, which roll along rails 908 and is movable between a first position at which the patient 903 on the bed 907 is subject to diagnosis by use of the slice image pick-up device 905 and a second position at which the patient 903 on the bed 907 is subject to therapy by use of the particle beam therapeutic apparatus 902.

The therapy/diagnosis is bed 907 has a top panel 909 on which the patient is made to lie. The top panel 909 is mounted so that it is movable and rotatable in the horizontal plane, and is movable up and down, and the image pick-up by use of the slice image pick-up device 905 and the irradiation by use of the particle beam therapeutic apparatus 902 are both possible.

The top panel 909 may be formed so that it is also capable of inclination.

Where the slice image pick-up device is an X-ray slice image pick-up device, the top panel 909 is preferably formed of a material of high transparency to X-rays such as glass fiber reinforced plastic. Where the slice image pick-up device is a nuclear magnetic resonance slice image pick-up device, the top panel is preferably formed of a non-magnetic material.

Prior to diagnosis and therapy, the patient is made to lie on the therapy/diagnosis table 907 and is made to assume a prescribed posture. The bed 907 is then moved to the slice image pick-up device 905, where the bed 907 is adjusted so that the position of the patient is most suitable for the image pick-up. By use of the slice image pick-up device 905, the location, shape and the like of the affected part is detected. After the slice image pick-up is completed, the table 907 is moved along the rail 908 to the particle beam therapeutic apparatus 902 and the bed 907 is moved so that the patient is most suitable for the radiation therapy using a particle beam such as an electron beam, proton beam, neutron beam, heavy particle beam or the like.

Since the bed is movable, the patient need not move for himself. The internal organs will not move between the slice image pick-up phase and radiation therapy phase.

In the embodiment described, the slice image pick-up device is an X-ray slice image pick-up device, However, a nuclear magnetic resonance slice image pick-up device, positron slice image pick-up device or the like may also be used.

The above described movable bed can also be provided to be movable between an X-ray positioning device (rather than the slice image pick-up device) and the therapeutic apparatus. The X-ray positioning device is used for the positioning in the directions perpendicular to the direction of the irradiation.

When the above described bed is used, it is not necessary to move the patient from one bed for the slice image pick-up to another bed for the particle beam therapy. The affected part as detected by the slice image pick-up device is easily made to align with the particle beam for the irradiation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A therapeutic apparatus comprising: irradiating means for irradiating an ionized particle beam;
a therapy table on which a patient is mounted;
X-ray computer tomography means for accumulating image data;
means responsive to said image data from said X-ray computer tomography means for generating a first image of at least part of the patient indicating the position of an affected part;
first display means for displaying said first image generated by said X-ray computer tomography means;
X-ray means for generating a second image of at least part of the patient indicating the position of said ionized particle beam, said second image being a center projection image formed on a plane when the patient is projected by an X-ray radiating from a point;
second display means for displaying said second image generated by said X-ray means;
input means for inputting positional information indicative of locations of reference points of physical characteristics in said first image and said second image, said physical characteristics being identified on said second image and the positions of said reference points being related to the position of said affected part;
computing means for calculating the distance of movement of the therapy table such that said ionized particle beam is irradiated onto said affected part of the patient on the basis of said positional information of said first image and said second image and for calculating the shape, dose, and energy of said ionized particle beam; and
means for moving the patient relative to said ionized particle beam on the basis of said calculated distance.

2. The apparatus of claim 1, wherein said physical characteristics comprises a bone.

3. The apparatus of claim 1, further comprising a range shifter for varying the energy of the ionized particle beam thereby to change the range of the ionized beam to coincide with the depth of the affected part.

4. A method of using a therapeutic apparatus comprising ionized particle beam irradiating means mounted along a vertical projection axis, a therapy table, X-ray computer tomography means, first display means, X-ray means, second display means, input means, computer means, and means for moving the therapy table means, comprising the steps of:
positioning a patient on the therapy table;
accumulating image data using the X-ray computer tomography means;
generating a first image of at least part of the patient indicating the position of an affected part;
displaying said first image on the first display means;
inputting a first set of reference marks, with the input means, indicative of locations of physical characteristics of said first image displayed on the first display means;
calculating the distances between said affected part and said first set of reference marks;
generating a second image, using the X-ray means, of at least part of the patient illustrating a position of the vertical projection axis, said second image being a center projection image formed on a plane when the patient is projected by an X-ray radiation from a point;
displaying said second image on the second display means;
inputting a second set of reference marks, with the input means, indicative of this locations of said physical characteristics of said second image displayed on the second display means, said physical characteristics being identified on said second image and the positions of said reference marks being related to the position of said affected part;
calculating a distance of movement of the therapy table using the computer means, such that said affected part and the vertical projection axis coincide, on the basis of said first and second reference marks and calculating the shape, dose and energy of an ionized particle beam to be irradiated on the patient;
moving the therapy table said calculated distance of movement; and
irradiating the patient with an ionized particle beam of said calculated shape, dose, and energy.

5. A therapeutic apparatus comprising:
irradiating means for irradiating an ionized particle beam;
a therapy table on which a patient is mounted;
first X-ray computer tomography means for accummulating image data;
means responsive to said image data from said first X-ray computer tomography means for generating a first image of at least part of the patient indicating the position of an affected part;
first display means for displaying said first image generated by said first X-ray computer tomography means;
second X-ray computer tomography means for generating a second image of at least part of the patient indicating the position of said ionized particle beam, said second image being a center projection image formed of a plane of the patient;
second display means for displaying said second image generated by said second X-ray computer tomography means;
input means for inputting positional information indicative of locations of reference points of physical characteristics in said first image and said second image, said physical characteristics being identified on said second image and the positions of said reference points being related to the positions of said affected part;
computing means for calculating the distance of movement of the therapy table such that said ionized particle beam is irradiated onto said affected part of the patient on the basis of said positional information of said first image and said second image and for calculating the shape, dose, and energy of said ionized particle beam; and
means for moving the patient relative to said ionized particle beam on the basis of said calculated distance.

6. A method of using a therapeutic apparatus comprising particle beam irradiating means mounted along a vertical projection axis, a therapy table, first X-ray computer tomography means, first display means, second X-ray computer tomography means, second display means, input means, computer means, and means for moving the therapy table means, comprising the steps of:
positioning a table on the therapy table;

accummulating image data using the first X-ray computer tomography means;

generating a first image of at least part of the patient indicating the position of an affected part;

displaying said first image on the first display means;

inputting a first set of reference marks, with the input means, indicative of locations of physical characteristics of said first image displayed on the first display means;

calculating the distances between said affected part and said first set of reference marks;

generating a second image, using the second X-ray computer tomography means, of at least part of the patient illustrating a position of the vertical projection axis, said second image being a center projection image formed on a plane of the patient;

displaying said second image on the second display means;

inputting a second set of reference marks, with the input means, indicative of the locations of said physical characteristics of said second image displayed on the second display means, said physical characteristics being identified on said second image and the positions of said reference marks being related to the position of said afected part;

calculating a distance of movement of the therapy table, using the computer means such that said affected part and the vertical projection axis coincide, on the basis of said first and second reference marks and calculating the shape, dose and energy of an ionized particle beam to be irradiated on the patient;

moving the therapy table said calculated distance of movement; and irradiating the patient with an ionized particle beam of said calculated shape, dose, and energy.

* * * * *